(12) United States Patent
Lingappa et al.

(10) Patent No.: US 6,593,103 B1
(45) Date of Patent: *Jul. 15, 2003

(54) HIV CAPSID ASSEMBLY-ASSOCIATED COMPOSITIONS AND METHOD

(75) Inventors: Jaisri R. Lingappa, San Francisco, CA (US); Vishwanath R. Lingappa, San Francisco, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/020,144

(22) Filed: Feb. 6, 1998

Related U.S. Application Data

(60) Provisional application No. 60/039,309, filed on Feb. 7, 1997.

(51) Int. Cl.$^7$ ................................................ C12P 21/06
(52) U.S. Cl. ........................ 435/68.1; 424/58; 424/74; 424/93.21; 424/93.7; 424/132.1; 424/725; 424/750; 435/6; 435/69.1; 435/70.1; 514/783; 536/23.1; 536/23.72; 800/320.3
(58) Field of Search .......................... 435/6, 68.1, 69.1, 435/70.1; 536/23.1, 23.72; 424/58, 74, 93.21, 93.7, 132.1, 725, 750; 514/783; 800/320.3

(56) References Cited

U.S. PATENT DOCUMENTS 5,324,637 A * 6/1994 Thompson et al. ......... 435/68.1

OTHER PUBLICATIONS

Lehninger et al. Priciples of Biochemistry (1993), 2nd. Ed. Worth Publishers Inc., New York, NY, pp. 483–485.*
Platt et al.; Characterization of human immunodeficiency virus type 1 Pr55gag membrane association in a cell–free system: requirement for a c–terminal domain. Proceedings of the National Academy of Sciences. vol 91 (1994) pp. 4594–4598.*
Geballe et al.; Variable inhibition of cell–free translation by HIV–1 transcript leader sequences. Nucleic Acid Research. vol. 20 (1992) pp. 4291–4297.*
Raju et al. Mammalian myristoyl CoA:protein N–myristoyl-tranferase. Molecular and Cellular Biochemistry. vol. 149/150 (1995) pp. 191–202.*
Bisbal et al., "Cloning and Characterization of a RNAse L Inhibitor. A New Component of the Interferon–Regulated 2–5A Pathway," *J. Biol. Chem.* 270(22):13308–13317 (1995).
Lingappa et al., "A Multi–Step, ATP–Dependent Pathway for Assembly of Human Immunodeficiency Virus Capsids in a Cell–Free Sysytem," *J. Cell Biol.* 136:567–581 (1997).
Lingappa et al., "A Eukaryotic Cytosolic Chaperonin Is Associated With a High Molecular Weight Intermediate in the Assembly of Hepatitis B Virus Capsid, a Multimeric Particle," *J. Cell Biol.* 125(1):99–111 (1994).
Sakalian et al., "Synthesis and Assembly of Retrovirus Gag Precursors into Immature Capsids In Vitro," *J. Virology* 70: 3706–375 (1996).
Spearman and Ratner, "Human Immunodeficiency Virus Type 1 Capsid Formation in Reticulocyte Lysates," *J. Virology* 70(11):8187–8194 (1996).
Weldon et al., "1998 Type D Retrovirus Capsid Assembly and Release are Active Events Requiring ATP," *J. Virology* 72:3098–3106 (1998).
Bisbal et al., *J. Biol. Chem.* 270 (22): 13308–133 17 (1995).
Lingappa et al., *J. Cell Biol.* 125 (1): 99–111 (1994).
Lingappa et al., *J. Cell Biol.* 136: 567–581 (1997).
Sakalian et al., *J. Virology* 70: 3706–3715 (1996).
Spearman et. al., *J. Virology* 70 (11): 8187–8194 (1996).
Weldon, et. al., *J. Virol.* 72: 3098–3106 (1998).

* cited by examiner

*Primary Examiner*—James Housel
*Assistant Examiner*—Ulrike Winkler
(74) *Attorney, Agent, or Firm*—Barbara Rae-Venter; Rae-Venter Law Group

(57) ABSTRACT

A cell-free method for translation and assembly of retroviral, particularly HIV, capsid and capsid intermediates is disclosed. Also disclosed are novel HIV capsid assembly intermediates and novel host proteins which bind to such assembly intermediates. The invention also includes a screening method for compounds that alter retrovirus capsid assembly, and a method of treating HIV using compounds which inhibit the HIV capsid assembly pathway.

11 Claims, 8 Drawing Sheets

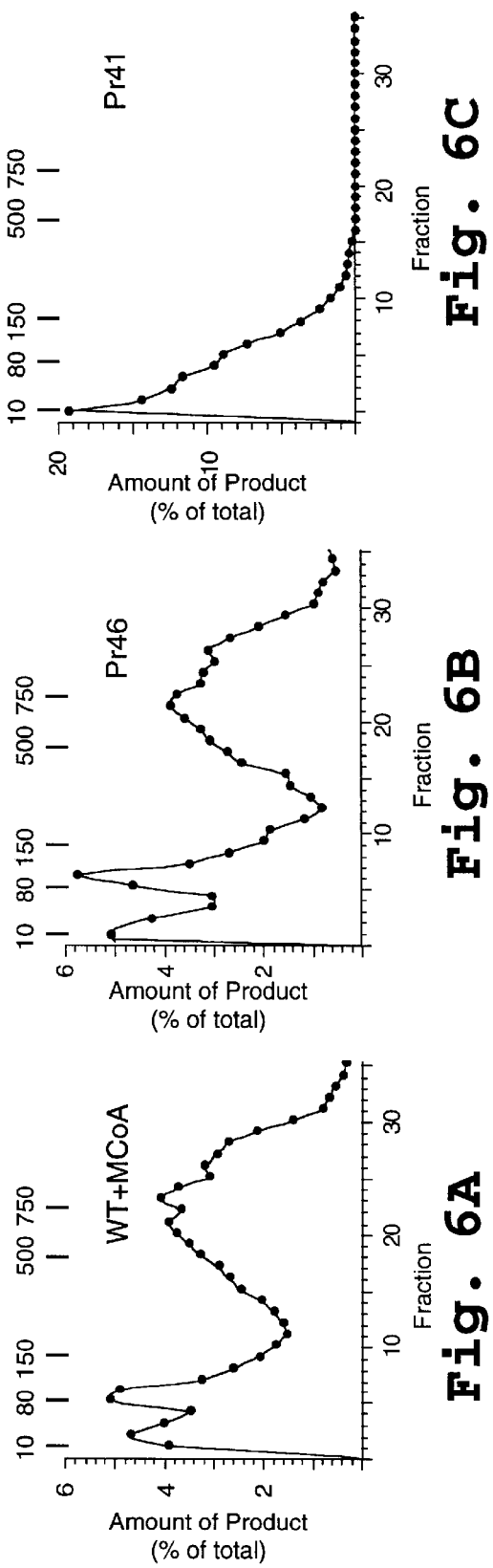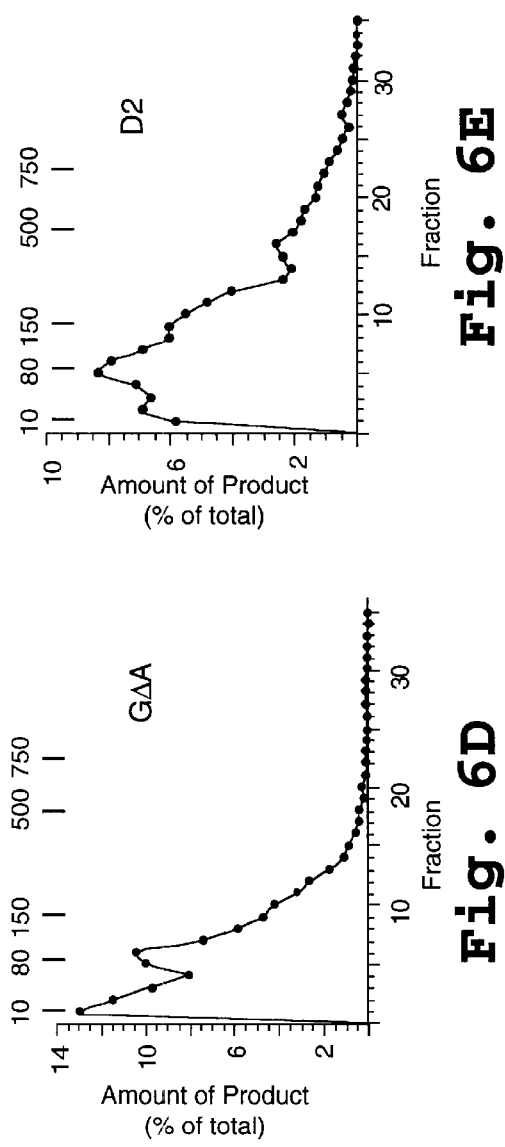

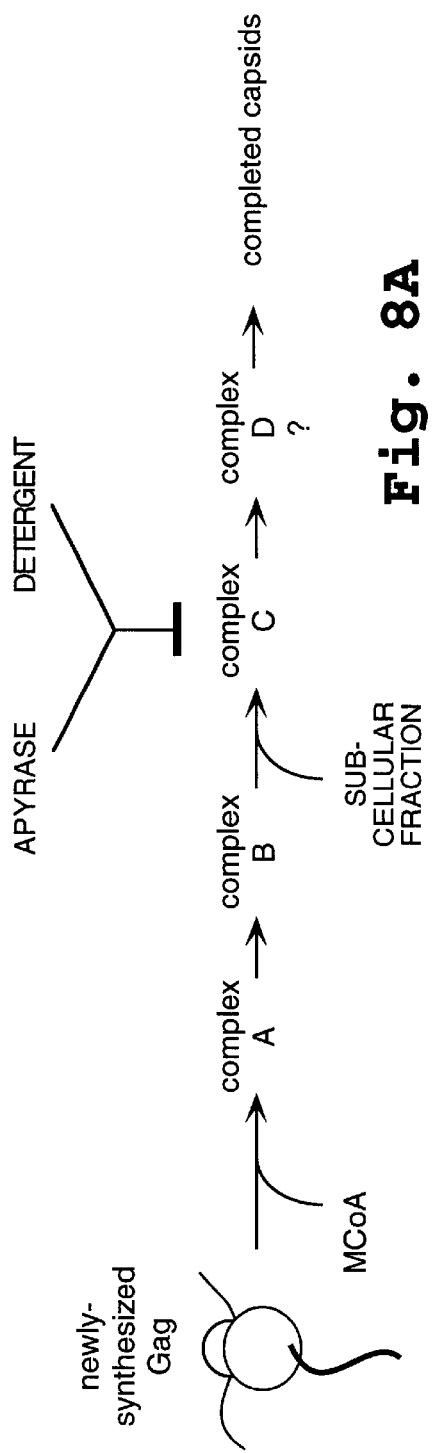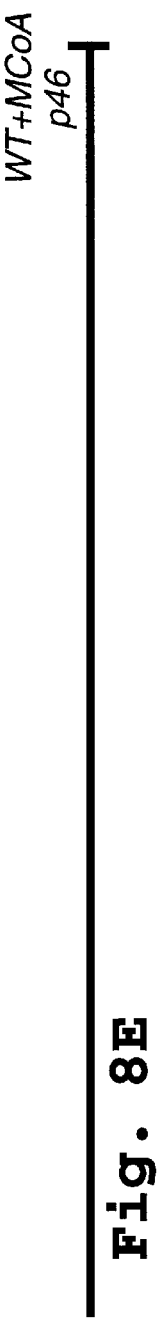

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1610 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (C) INDIVIDUAL ISOLATE: DNA coding sequence for HIV
         capsid protein Pr55

(xi) SEQUENCE DESCRIPTION: SEQ ID NO:1:

```
ATGGGTGCGA GAGCGTCGGT ATTAAGCGGG GGAGAATTAG ATAAATGGGA AAAAATTCGG      60

TTAAGGCCAG GGGGAAAGAA AAAATATAAG TTAAAACATA TAGTATGGGC AAGCAGGGAG     120

CTAGAACGAT TCGCAGTCAA TCCTGGCCTG TTAGAAACAT CAGAAGGCTG CAGACAAATA     180

TTGGGACAGC TACAGCCATC CCTTCAGACA GGATCAGAAG AACTTAGATC ATTATATAAT     240
```

-continued

```
ACAGTAGCAA CCCTCTATTG TGTACATCAA AGGATAGATG TAAAAGACAC CAAGGAAGCT     300

TTAGAGAAGA TAGAGGAAGA GCAAAACAAA AGTAAGAAAA AGGCACAGCA AGCAGCAGCT     360

GCAGCTGGCA CAGGAAACAG CAGCCAGGTC AGCCAAAATT ACCCTATAGT GCAGAACCTA     420

CAGGGGCAAA TGGTACATCA GGCCATATCA CCTAGAACTT TAAATGCATG GGTAAAAGTA     480

GTAGAAGAAA AGGCTTTCAG CCCAGAAGTA ATACCCATGT TTTCAGCATT ATCAGAAGGA     540

GCCACCCCAC AAGATTTAAA CACCATGCTA AACACAGTGG GGGGACATCA AGCAGCCATG     600

CAAATGTTAA AAGAGACTAT CAATGAGGAA GCTGCAGAAT GGGATAGAGT GCATCCAGTG     660

CATGCAGGGC CTATTGCACC AGGCCAAATG AGAGAACCAA GGGGAAGTGA CATAGCAGGA     720

ACTACTAGTA CCCTTCAGGA ACAAATAGGA TGGATGACAA ATAATCCACC TATCCCAGTA     780

GGAGAAATCT ATAAAAGATG GATAATCCTG GGATTAAATA AAATAGTAAG AATGTATAGC     840

CCTACCAGCA TTCTGGACAT AAGACAAGGA CCAAAGGAAC CCTTTAGAGA TTATGTAGAC     900

CGGTTCTATA AAACTCTAAG AGCCGAACAA GCTTCACAGG ATGTAAAAAA TTGGATGACA     960

GAAACCTTGT TGGTCCAAAA TGCAAACCCA GATTGTAAGA CTATTTTAAA AGCATTGGGA    1020

CCAGCAGCTA CACTAGAAGA AATGATGACA GCATGTCAGG GAGTGGGGGG ACCCGGCCAT    1080

AAAGCAAGAG TTTTGGCTGA AGCCATGAGC CAAGTAACAA ATCCAGCTAA CATAATGATG    1140

CAGAGAGGCA ATTTTAGGAA CCAAAGAAAG ACTGTTAAGT GTTTCAATTG TGGCAAAGAA    1200

GGGCACATAG CCAAAAATTG CAGGGCCCCT AGGAAAAAGG GCTGTTGGAG ATGTGGAAGG    1260

GAAGGACACC AAATGAAAGA TTGCACTGAG AGACAGGCTA ATTTTTTAGG GAAGATCTGG    1320

CCTTCCTACA AGGGAAGGCC AGGGAATTTT CTTCAGAGCA GACCAGAGCC AACAGCCCCA    1380

CCAGAAGAGA GCTTCAGGTT TGGGGAGGAG AAAACAACTC CCTCTCAGAA GCAGGAGCCG    1440

ATAGACAAGG AACTGTATCC TTTAACTTCC CTCAGATCAC TCTTTGGCAA CGACCCCTCG    1500

TCACAATAAG GATAGGGGGG CAACTAAAGG AAGCTCTATT AGATACAGGA GCAGATGATA    1560

CAGTATTAGA AGAAATGAAT TTGCCAGGAA AATGGAAACC AAAAATGATA              1610
```

(2) INFORMATION FOR SEQ ID NO:2:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (vi) ORIGINAL SOURCE:
        (C) INDIVIDUAL ISOLATE: peptide fragment of host
            cell (wheat germ) protein HP68

(xi) SEQUENCE DESCRIPTION: SEQ ID NO:2:

```
Pro Arg Pro Tyr Leu Asp Val Lys Gln Arg Leu Lys Ala Ala Arg Val
 1               5                  10                  15

Ile Arg Ser Leu Leu Arg Ser Asn
            20
```

HIV CAPSID ASSEMBLY-ASSOCIATED COMPOSITIONS AND METHOD

This application claims the priority of U.S. Provisional Application No. 60/039,309, filed Feb. 7, 1997, which is pending as of the filing date of the present application, and which is incorporated herein by reference.

The work described herein was supported in part by United States government grant K08AI01292 from the National Institutes of Health (NIH). Accordingly, the United States Government has certain rights in this invention.

FIELD OF THE INVENTION

The invention is concerned with a method for producing HIV capsids in a cell-free extract. Also described are capsid intermediate compositions, auxiliary proteins, and screening assays that measure the ability of drugs to inhibit this process.

REFERENCES

Bryant, M., et al., *Proc. Natl. Acad. Sci.* 87:523–527 (1990).
Dubochet, J., et al., *J. Ultrastruct. Res.* 35:147–167 (1971).
Ericksons, A. H., and Blobel, G., *Methods Enzymol.* 96:38–50 (1983).
Facke, M., et al., *J. Virol.* 67:4972–4980 (1993).
Forsayeth, J. R. and Garcia, P. D., *Biotechniques* 17:354–358 (1994).
Gelderblom, H. R., *AIDS* 5:617–638 (1991).
Gheysen, D., et al., *Cell* 59:103–112 (1989).
Gottlinger, H. G., et al., *Proc. Natl. Acad. Sci.* 86:5781–5785 (1989).
Hockley, D. J., et al., *J. Gen. Virol.* 75:2985–2997 (1994).
Hynes, G., et al., *Electrophoresis* 17: 1720–1727 (1996).
Jacobs, E., et al., *Gene* 79:71–81 (1989).
Jowett, J. B. M., et al., *J. Gen. Virol.* 73:3079–3086 (1992).
Lingappa, J. R., et al., *J. Cell. Biol.* 125:99–111 (1984).
McEwen, C. R., Anal. *Biochem.* 20:114–149 (1967).
Melton, D. A., et al., *Nucleic Acids Res.* 12:7035–7056 (1984).
Mergener, K., et al., *Virology* 186:25–39 (1992).
Merrick, W. C., *Methods Enzymol.* 101:606–615 (1983).
Platt, E. J. and Haffar, O. K., *Proc. Natl. Acad. Sci.* 91:4594–4598 (1994).
Royer, M., et al., *Virology* 184:417422 (1991).
Sambrook, J., et al., in *MOLECULAR CLONING, A LABORATORY MANUAL*, Cold Spring Harbor Laboratory Press, Cold Spring Harbor, N.Y. (1989).
Smith, A. J., et al., *J. Virol.* 67:2266–2275 (1993).
Spearman, P., et al., *J. Virol.* 68:3232–3242 (1994).
Spirin, A. S., et al., *Science*, 242: 1162–1164 (1988).
Towler, D. A., et al., *Ann. Rev. Biochem.* 57:69–99 (1988).
Trono, D., et al., *Cell* 59:113–120 (1989).
Walter, P. and Blobel, G., *Proc. Natl. Acad. Sci. USA* 77:7112–7116 (1980).
Walter, P. and Blobel, G., *Cell* 34:525–533 (1983).
Wang, C.-T. and Barklis, E., *J. Virol.* 67:4264–4273 (1993).
Wills, J. W. and Craven, R. C., *AIDS* 5:639–654 (1991).
Willison, K., et al., *Cell* 57: 621–632 (1989)
Zhao, Y., et al., *Virology* 199:403–408 (1994).

BACKGROUND OF THE INVENTION

The protein shell of the HIV virion, termed the HIV capsid or core, is composed of approximately 1500 copies of the Pr55 Gag structural protein precursor (Gelderblom, 1991). For proper assembly of the capsid to occur, Pr55 chains must undergo myristoylation (Gheysen, et al., 1989; Gottlinger, et al., 1989), an N-terminal modification thought to occur co-translationally (Towler, et al., 1988). The myristoylated chains are targeted to the host plasma membrane where assembly takes place concomitant with RNA encapsidation. As capsids are formed, they bud into the plasma membrane. This results in envelopment and subsequent release of viral particles from the cell. Coincident with their release, the immature viral particles undergo a maturation process, involving proteolytic processing of the precursor structural proteins and condensation of the capsids into collapsed, electron-dense cores (Gelderblom, 1991; Wills and Craven, 1991).

The manner in which HIV capsids assemble differs from that of many other retroviruses. Other retroviruses of the type B and type D category assemble "preformed" capsids in the cytoplasm of the infected cells. Such preformed capsids are then transported to other areas of the cell, such as the plasma membrane. In contrast, HIV capsids and other type C retroviruses form in intimate association with the plasma membrane, as described above. This important characteristic of HIV capsid formation has been demonstrated through electron microscopic studies (reviewed by Gelderblom, 1991; Wills and Craven, 1991).

Analyses of various mutants of Pr55 have revealed key domains required for efficient capsid assembly and targeting to the plasma membrane (see for example Gheysen, et al., 1989; Gottlinger, et al., 1989; Trono, et al., 1989; Royer, et al., 1991; Jowett, et al., 1992; Facke, et al., 1993; Wang and Barklis, 1993; Spearman, et al., 1994; Hockley, et al., 1994; Zhao, et al., 1994). However, the actual mechanisms involved in coordinating the formation of an HIV capsid from 1500 Gag monomers have not been elucidated. Many important questions about HIV capsid assembly remain unanswered, including whether assembly is an energy-dependent process, whether host proteins are required for assembly to take place, and whether assembly proceeds by way of discrete intermediates.

A major obstacle to addressing these questions experimentally has been the inherent difficulty of studying capsid assembly in cellular systems. In cells, many of the events in question proceed extremely rapidly and are not readily amenable to manipulation, making it difficult to identify trans-acting factors and energy substrates that may be required for assembly.

Development of a cell-free system that recreates capsid biogenesis would greatly facilitate a biochemical dissection and mechanistic understanding of capsid formation. Moreover, such a system would be useful as a screening assay for identifying drugs that interfere with the process.

It is the discovery of the present invention that immature HIV capsids can be assembled in a cell-free protein translation system, when certain key components are added to the reaction. Capsid formation by this method has the same requirement as capsid formation in vivo, including a requirement for myristoylation of Gag and an apparent requirement for membranes. Furthermore, in the present invention, this method for cell-free assembly of HIV capsids is used to reveal the existence of previously unknown steps in HIV virus formation. This system has now been used to demonstrate that capsid formation is dissociable into co- and post-translational phases, each of which has distinct co-factor and/or energy requirements. The reactions that occur during the post-translational phase are dependent on ATP and at least two independent host factors which are distinguished by their differential sensitivities to non-ionic detergents. This system can be used as a screening assay or selection assay for identification of new compounds that interfere with capsid formation, and hence with production of infectious virus.

Included in this invention is the discovery that formation of HIV capsids proceeds by way of a pathway of previously unrecognized assembly intermediates, in both cells and in the cell-free system. Such intermediates have utility, for example, in the design of drugs (including peptides and antibodies) and vaccines that interfere with progression from one intermediate to the next, in the design of drugs that act by inhibiting host cell machinery involved in capsid formation, and in the design of assay systems that examine the efficacy and mechanism of action of drugs that inhibit capsid formation.

In a related aspect, also forming part of the invention are host proteins that are involved in HIV capsid formation. An exemplary host protein, termed HP68, is a 68 kD protein present in a cell-free fraction of wheat germ extract and which forms part of one or more of the intermediate complexes described above. This protein is useful as a component of the cell-free translation systems and methods described above. It has further utility in the design of drugs that block or alter its association with HIV Gag and which therefore prevent formation of immature HIV capsids.

Forming yet another related aspect of the present invention, is the discovery that pieces of genomic HIV RNA can be encapsidated into the HIV capsids produced in the cell-free system by adding such RNA to the system. This feature of the invention can be used to design of drugs that interfere with encapsidation and in the design of assay systems that examine the mechanism of actions of drugs that inhibit encapsidation.

SUMMARY OF THE INVENTION

In one aspect, the present invention is concerned with a cell-free system for translation and assembly of retroviral capsids and capsid intermediates. In particular, the invention includes a cell-free system for translation/assembly of capsids and capsid intermediates of human immunodeficiency virus (HIV).

The cell-free translation system includes (i) a cell-free translation mixture, (ii) an mRNA molecule encoding a Gag Pr55 protein derived from human immunodeficiency virus (HIV), (iii) myristoyl coenzyme A, (iv) a detergent-sensitive fraction derived from eukaryotic cell membranes, and (iv) a eukaryotic cell component characterized by insensitivity to a concentration of at least 0.5% (wt/vol) "NIKKOL" detergent.

Generally, in this context, the cell-free translation mixture includes sufficient cellular machinery and components to support protein translation—transfer RNA, ribosomes, a full complement of at least 20 different amino acids and an energy source, which may be ATP and/or GTP, as discussed herein. While the cell-free translation mixture be derived from any of a number of cell types known in the art, in a preferred embodiment, the cell-free extract in the mixture is a wheat germ extract. In another preferred embodiment, the system is also charged with HIV genomic RNA or a fraction thereof, in which case the system is capable of making capsids with such RNA encapsidated within. In yet another preferred embodiment, the system can be supplemented with additional or exogenous host cell protein, such as HP 68 described herein, that is involved in the assembly complex formation.

This system, in any of its embodiments, may also be used to prepare capsid intermediates from HIV mutants that are defective in capsid assembly. Such mutants include, but are not limited to Pr46, Pr41, GΔA, and D2, which are known in the art.

In still another preferred embodiment, the translation system is a coupled transcription-translation system, in which case it further includes (i) a DNA molecule which encodes HIV Gag Pr55, (ii) an RNA polymerase for synthesizing said mRNA, and (iii) sufficient concentrations of nucleotides ATP, UTP, GTP, and CTP to support the mRNA synthesis.

In a related embodiment, the invention includes a method of producing an HIV capsid intermediate in a cell-free system. According to this embodiment of the invention, the translation system described above, in any of its embodiments, charged with an mRNA molecule encoding an HIV Pr55 Gag protein is incubated for a period of time sufficient to assemble Gag Pr55 mRNA translation products into an immature HIV capsid.

In another related embodiment, the invention includes an isolated HIV capsid intermediate selected from a group of HIV capsid intermediates having buoyant densities selected from the group of about 10 S, about 80 S, about 150 S and about 500 S, as described herein. Such intermediates have utility, for example as components in screening assays for compounds which interfere with HIV capsid assembly. Such intermediates may include host cell proteins, such as HP 68 or homologs thereof, as described herein.

In still another related embodiment, the invention includes a method of selecting a compound capable of altering HIV capsid assembly, i.e., a screening method. The method includes adding a test compound to a reaction mixture which includes the following components: (i) a cell-free translation mixture that includes a cellular extract, tRNA, ribosomes, amino acids and an energy source, (ii) an mRNA molecule encoding HIV Gag Pr55, (iii) myristoyl coenzyme A. Preferably, the myristoyl coenzyme A is present at a concentration greater than about 0.1 micromolar in the assay. The amount of capsid assembly is then measured compared in the absence and presence of test compound. A compound is selected as a compound capable of altering HIV capsid assembly if this comparison yields a significant differences between the measured amounts of either capsid or capsid intermediate(s) formed.

In still another related embodiment, the invention includes a protein that is identified as being involved in capsid assembly, as evidenced by its association with capsid intermediates, especially intermediates B, C, and D, as described herein. Generally the protein is characterized as having a peptide region having the sequence presented as SEQ ID NO: 2, specific immunoreactivity with monoclonal antibody 23c, and an apparent molecular weight of about 68 kilodaltons. Preferably, the protein is characterized by at least 75% amino acid sequence identity to HP 68. In an exemplified embodiment, it is derived from wheat germ extract, and is identified as HP 68. It is appreciated, however, that such a protein can derived from any of a number of host cell sources, including, but not limited to human cells. The present invention teaches how to identify such other, homologous proteins.

In still a further related embodiment, the invention includes a method of inhibiting HIV capsid formation in a cell. The method includes adding to the cell a compound that has been selected for its ability to inhibit capsid formation or formation of capsid intermediate(s) in any embodiment of the cell-free translation system described herein. As a related feature, the invention also extends to provide a method of selecting compounds effective to alter HIV capsid formation in cells. According to this feature of the invention, the test compound is added to cells that are forming HIV retroviral capsids. The quantity and nature of capsid intermediates formed is measured and compared to capsids formed in control cells. The compound is selected if if the quantity or nature of intermediates measured in the presence of the compound is significantly different than the those formed in the absence of the compound. Association of host assembly protein HP 68 with capsid intermediates can be used as a measurement in such a selection method, as well.

In still a further related embodiment, the invention includes a method of encapsidating genomic HIV RNA or fragments thereof. Here, any of the embodiments of the cell-free translation system described herein are used. Genomic HIV RNA or RNA fragment is added to such a system, and is encapsidated during the reaction process.

These and other objects and features of the invention will become more fully apparent when the following detailed description of the invention is read in conjunction with the accompanying drawings.

BRIEF DESCRIPTION OF THE FIGURES

FIGS. 6(A–E) shows plots of pulse-chase experiments in which transcripts of different assembly-defective mutants Pr46 (6B), Pr41 (6C), GΔA (6D), and D2 (6E) and wild-type HIV (WT; 6A) were analyzed for assembly in a cell-free system; FIGS. 8(A–E) shows a schematic model for assembly of immature HIV capsids (8A) and the points along the pathway at which Gag mutants p41 (8B), GΔA or wild-type in the absence of MCoA (Wt–MCoA; 8C), D2 (8D) are arrested, compared to wild type in the presence of MCoA (WT+MCoA) or p46 (8E).

DETAILED DESCRIPTION OF THE INVENTION

I. Definitions

Figure 1A:
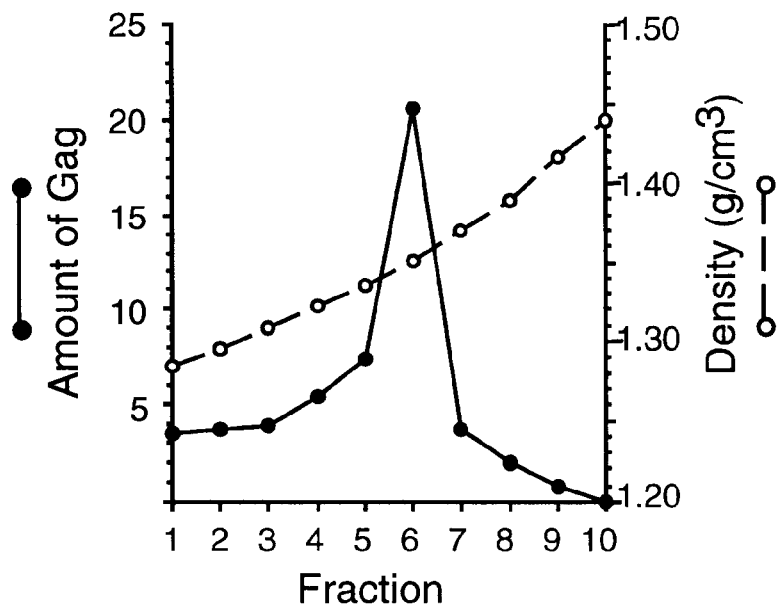
FIGS. 1A and 1B show migration of capsids formed in a cell free system (1A) and in a cellular system (1B) on velocity sedimentation gradients, in the form of plots of the buoyant density of each of the sequential fractions collected, assessed by refractive index (open circles), and of the amount of Gag protein in each fraction, as assessed by densitometry (closed circles)

As defined herein the term "cell-free translation" refers to protein synthesis carried out in vitro in a cell extract that is essentially free of whole cells.

The term "cell-free translation mixture" refers to any of a number of cell-free translation 20 mixtures or systems commercially available or known in the art, including continuous flow systems (See, e.g., Erickson and Blobel, 1983; Spirin, et al., 1988; Merrick, 1993). Generally, this will include a cell extract (made from any cells) that contains ribosomes and other factors required for protein synthesis, which is supplemented with a full complement of amino acids, ATP, GTP, and, usually, an energy regenerating system, such as creatine phosphate and creatine phosphokinase. The mixture which is capable of supporting protein synthesis when an mRNA encoding a protein is added. Cell-free translation mixtures are commercially available, for example from Promega Biotech (Madison, Wis.).

The term "detergent-sensitive fraction" refers to a lipid component derived from cell membranes such as can be isolated from some cell-free extracts, that is inactivated by treatment with a non-ionic detergent such as NP40. In the context of the present invention, the term refers to a component most likely containing a membrane lipid bilayer that is present in a standard wheat germ extract prepared according to the methods described by Erickson and Blobel (1983), which component is deactivated with reference to supporting HIV capsid assembly when a concentration of 0.1% (wt/vol) "NIKKOL" is added to the extract. It is appreciated that such a detergent-sensitive factor can be present in extracts of other cells similarly prepared, or can be prepared independently from a separate cell extract, and then added to a cell-free translation system.

The term "eukaryotic cell component characterized by insensitivity to at least 0.5% NIKKOL" refers to a high speed pellet of a eukaryotic cell extract, prepared and detergent-extracted as described with particular reference to wheat germ cells in Example 2.

The term "high speed wheat germ extract supernatant" refers to the supernatant formed when an S23wheat germ extract is further centrifuged at about 100,000×g for 15 minutes. It is appreciated that extracts of other eukaryotic cells, such as rabbit reticulocytes may be used to form analogous high speed supernatants, and that such supernatants will be useful in practicing the present invention.

The term "assembly intermediates" refers to capsid substructures (composed of Gag polypeptides as well as other, as-yet-undefined components) that must be formed in an ordered sequence in order for the final completed capsid structure to be made.

The term "assembly pathway" refers to the ordered set of serial assembly intermediates required for formation of the final completed capsid structure. To progress from one assembly intermediate to the next, a specific modification or modifications of the intermediate must take place. These modifications are as yet undefined and are likely to include:

addition of more Gag polypeptides, host-mediated modifications of the intermediate, and association with host factors.

The term "programmed with mRNA derived from HIV or from HIV mutant" means, in the context of the present invention, addition to a cell-free translation mixture or cells, mRNA that encodes the wild-type or mutant capsid protein Gag, or by adding to cells a DNA that specifies the production of such a wild-type or mutant Gag in RNA. mRNA can be added to cells directly, such as by transfection or electroporation according to methods well known in the art. DNA that directs the production of mRNA can also be "added to cells" by inserting the corresponding gene into an appropriate vector and transfecting the cell. Likewise, mRNA can be added directly to a cell-free translation mixture or can be produced in the mixture in a coupled transcription-translation reaction.

The term "HIV capsid" refers to an ordered icosahedral particle composed of approximately 1500 Gag polypeptides within which is normally housed HIV specific genomic material and enzymes. The capsid is first formed as an immature structure, and later undergoes a "maturation" event mediated by the HIV-specific protease. The protease cleaves the Gag polypeptides that form the immature capsid into smaller proteins. This results in a change in the shape of the capsid to the mature, bullet shaped capsid. Note that an immature capsid must be formed first before a proper mature capsid is made. Maturation normally happens very quickly after the immature capsid is formed.

The term "75% homology" or "75% identity" when used in conjunction with protein or nucleotide sequences, means that a sequence exhibits at least about 75% identity to a reference sequence, when the two are compared by any of a number of algorithms designed to compare protein or nucleic acid sequences.

II. Cell-free Translation/Assembly System

The present invention includes a cell-free translation/assembly system that is capable of supporting assembly of immature capsids formed from Human Immunodeficiency Virus (HIV) Gag Pr55 protein subunits. According to the discovery of the present invention, the system contains the following components: cell-free translation extract, mRNA encoding the HIV Gag Pr55 protein, an ATP regenerating energy source, specific quantities of ATP and myristoyl coenzyme A, a defined, detergent-sensitive fraction likely to consist of membrane fragments or components, and a detergent-insensitive eukaryotic cell component. The reaction mixture may be additionally enriched by addition of a host protein which is involved in assembly formation, exemplified by HP68, below. These latter three components may be derived from cells used to make the extract that is then used for cell-free translation. The importance of these features of the cell-free translation/assembly system will be appreciated with further reference to the description that follows.

A. Components of Cell-free Translation/Assembly System.

1. Cell-Free Protein Translation Mixture

The HIV translation/assembly system described herein contains a cell-free protein translation mixture. Known in the art are a number of such systems, the basic requirements of which have been well-studied (Erickson and Blobel, 1983; Merrick, 1983). Examples include wheat germ extract and rabbit reticulocyte extract, available from commercial suppliers such as Promega (Madison, Wis.), as well as high speed supernatants formed from such extracts, as described herein. Such systems include, in addition to the cell-free extract containing translation machinery (transfer RNA, ribosomes), an energy source (ATP, GTP) and a full complement of (at least 20 different) amino acids. Methods known in the art are used to maintain energy levels sufficient to maintain protein synthesis, for example, by adding additional nucleotide energy sources during the reaction or by addition of of an energy source, such as creatine phosphate/creatine phosphokinase. The ATP and GTP present in the standard translation mixture, generally between about 0.1 and 10 mM, more preferably between about 0.5 and 2 mM, are sufficient to support both protein synthesis and capsid formation, which may require additional energy input. Generally, the reaction mixture prepared in accordance with the present invention, as exemplified in Example 1, can be titered with a sufficient amount of ATP or GTP to support production of a concentration of about 10 picomolar Gag in the system. The translation mixture may also include the detergent-sensitive, detergent-insensitive, and host protein fractions described in Parts 4–6, below, or it may be supplemented with such fractions.

Example 1 provides methodological details of an exemplary HIV capsid translation/assembly system prepared from wheat germ extract. According to an important discovery of the present invention, translation and assembly of HIV capsids are observed in greater yield, when a high speed supernatant derived from eukaryotic cell extracts is used as a translation mixture, as described in Example 2. Other components of the system are described in the sections that follow.

2. mRNA Encoding Gag Pr55 Protein

The cell-free translation reaction is initiated by adding HIV Gag Pr55 mRNA, the sequence of which is known in the art, or can be derived from the DNA sequence provided herein as SEQ ID NO: 1. Suitable mRNA preparations include a capped RNA transcript produced in vitro using the mMESSAGE mMACHINE kit-(Albion). mRNAs can also be generated in the same reaction vessel as is used for the translation reaction by addition of SP40 polymerase to the reaction mixture, along with the HIV Gag coding region or cDNA. This coding region encoding Gag Pr55 can be obtained, for example, by DNA synthesis according to standard methods, using the sequence provided as SEQ ID NO: 1.

3. Myristoyl Coenyzme A

According to an important feature of the present invention, the cell-free translation mixture is supplemented with myristoyl coenzyme A. While the concentration required will vary according to the particular experimental conditions, in experiments carried out in support of the present invention, it was found that a concentration between about 0.1 and 100 micromolar, and preferably between about 5 and 30 micromolar supports HIV capsid formation. Without committing to a particular theory concerning the mechanism of the reaction, it is likely that this supplement promotes myristoylation of the Gag translation product and attachment to membrane fragment(s) present in the reaction mixture.

4. Detergent-sensitive Fraction

It has also been found that assembly of the HIV capsid is sensitive to non-ionic detergent above but not below the critical micelle concentration. This observation is consistent with a role for membranes being required at a particular step in capsid assembly.

5. Detergent-insensitive EukarEotic Cell Component

According to another important feature of the invention, HIV capsid assembly requires the presence of a cellular component that has a sedimentation value greater than 90 S in a sucrose gradient and is insensitive to extraction with at least 0.5% "NIKKOL".

6. Host Assembly Protein

According to another feature of the invention, a host cell-derived assembly protein may be involved in capsid formation. The presence of such a protein in a cell extract is detected by any of a number of means, including but not limited to immunoprecipitation of the complex, as described in Example 4. Alternatively, the protein, such as HP 68 can be added exogenously to the system. In studies carried out in support of the present invention, an exemplary host cell assembly protein was found in certain of the capsid complexes described below. This exemplary host cell protein is identified as HP68 and is characterized by (i) immunoreactivity with TCP-1 monoclonal antibody 23c (Inst. for Cancer Research, London, UK; Stressgen, Vancouver, B.C., Canada), and (ii) containing the peptide sequence SEQ ID NO: 2 (PRPYLDVKQRLKAARVIRSLLRSN). It is further characterized by a molecular weight of 68,000 (as assessed by SDS-PAGE). This protein is distinct from the "detergent insensitive fraction" described in the previous section, as evidenced by the ability of a high speed supernatant of wheat germ extract to block immunoprecipitation of complexes by monoclonal antibody 23c. It is the discovery of the present invention that HP68 and homologs thereof are cellular agents involved in capsid assembly, and that blockade of its reactivity may provide new therapeutic regimens for blocking HIV production.

1. Translation of Gag Pr55 Protein in a Cell-free System

The cell-free translation/assembly system of the invention contains the components described in Part.A, above. Example 1 provides details of an exemplary system derived from wheat germ extract, which is capable of supporting translation and assembly of HIV capsids. Briefly, protein synthesis is initiated in the cell-free translation/assembly system by adding an mRNA that encodes Gag Pr55 protein. Alternatively, when the system includes transcription means, such as SP6 or T7 polymerase, the reaction may be initiated by addition of DNA encoding the protein. Complete synthesis of protein and assembly into capsids is usually achieved within about 150 minutes.

Figure 1B:
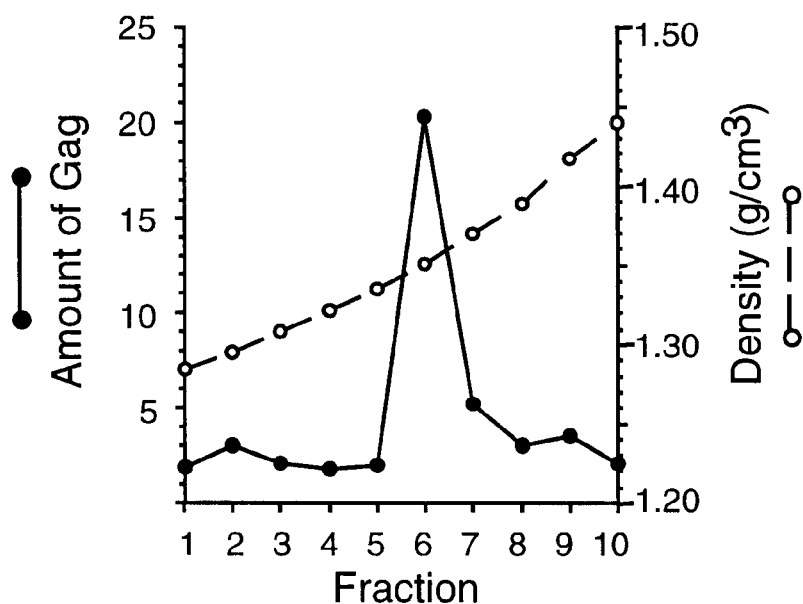

FIG. 1 shows that capsids formed in the cell-free system of the invention are substantially the same as those formed in cells. Shown in the figure is a comparison of migration of the capsids through an isopycnic CsCl gradient, where capsids formed in the cell-free translation/assembly system are shown in FIG. 1A, and capsids formed in transfected Cos cells are shown in FIG. 1B. Cell-free translation and assembly reactions containing 10 $\mu$M MCoA and $^{35}$S methionine were programmed with HIV Gag transcript and incubated under the conditions detailed in Example 1. At the end of the reaction, samples were diluted into buffer containing 1% NP40 (a non-ionic detergent), and separated into soluble and particulate fractions on sucrose step gradients, according to standard methods known in the art employing sucrose step or linear gradients as appropriate. The particulate fraction was collected and analyzed by velocity sedimentation on a 13-ml 15–60% linear sucrose gradient (Beckman SW40 Ti rotor, 35,000 rpm, 75–90 min). Fractions from the gradient were collected and subjected to sodium lauryl sulfate polyacrylamide gel electrophoresis (SDS-PAGE) analysis according to standard methods.

A parallel analysis of the particulate fraction was performed by subjecting the particulate fraction to CsCl gradient separation (2 ml isopycnic CsCl, 402.6 mg/ml; 50,000 rpm in a Beckman TLA 100 centrifuge) according to standard methods. Fractions were collected and assessed for Gag translation product (Pr55) (top of gradient is fraction 1, open circles, FIG. 1B). The fractions containing radiolabeled Pr55 were also subjected to SDS PAGE analysis; Gag content of the various fractions was estimated by scanning densitometry of autoradiographs made from the gels. Both conditions produced identical radiolabeled protein bands under these conditions. Material in the particulate fraction (>500-S) was further analyzed by a variety of methods as described below.

Translation of the HIV Gag transcript encoding Pr55 in the cell-free system resulted in the synthesis of approximately 2 ng Pr55 protein per microliter translation reaction. It is appreciated that increased production might be achieved, for example, by employing a continuous flow translation system (Spirin, et al., 1988) augmented with the specific factors and components described above.

By way of comparison, cell culture medium was collected from transfected Cos cells producing and releasing immature HIV particles. Virus particles were harvested by ultracentrifugation through a 20% sucrose cushion. Authentic immature capsids were generated by treating these harvested particles with detergent to remove their envelopes. These authentic capsids were sedimented on a velocity sedimentation gradient, in parallel with the particulate fraction of the cell-free reaction shown in FIG. 1A. Pr55 present in these fractions was visualized by immunoblotting.

Detergent-treated capsids generated in the cell-free system and detergent-treated (de-enveloped) authentic capsids behaved as a relatively homogenous population of particles of approximately 750-S (compare FIGS. 1A and 1B), with a buoyant density of 1.36 g·cm-3. Additionally, cell-free-assembled capsids and the authentic standard were identical in size as judged by gel filtration. Electron microscopic analysis revealed that capsids made in the cell-free system were morphologically similar to authentic capsids released from transfected cells and had the expected diameter of approximately 100 nm (Gelderblom, 1991). Thus, radiolabeled Pr55 protein synthesized in the cell-free system assembles into particles that closely resemble authentic immature HIV capsids generated in transfected cells, as judged by EM appearance as well as the biochemical criteria of size, sedimentation coefficient, and buoyant density.

The cell-free capsid assembly reaction described above can be extended to include packaging of RNA, by addition of genomic HIV RNA or fragments thereof during the capsid assembly reaction. Addition and monitoring of RNA encapsidation provides an additional parameter of HIV particle formation that can be exploited in drug screening assays, in accordance with the present invention.

The HIV RNA sequence to be used for making the HIV genomic RNA fragment can be selected from the 5' portion of the HIV genome, for example HIV at nt 455–1514. Although there are many permutations of HIV genomic sequences, an exemplary sequence in this regard is identified as GENBANK nucleotide identification number (NID) g326382. The sequence will preferably be greater than about 1,000 nucleotides in length and will be subcloned into a transcription vector. A corresponding RNA molecule is then produced by standard in vivo transcription procedures. This is added to the reaction mixture described above, at the beginning of the incubation period. Although the final concentration of RNA molecule present in the mixture will vary, the volume in which such molecule is added to the reaction mixture should be less than about 10% of the total volume.

III. Requirements of Capsid Assembly

According to important aspects of the invention, proper HIV capsid assembly in a cell-free system requires, in addition to competent protein synthetic machinery, certain components and processes described herein.

1. Myristoylation of Pr55

Figure 2A:
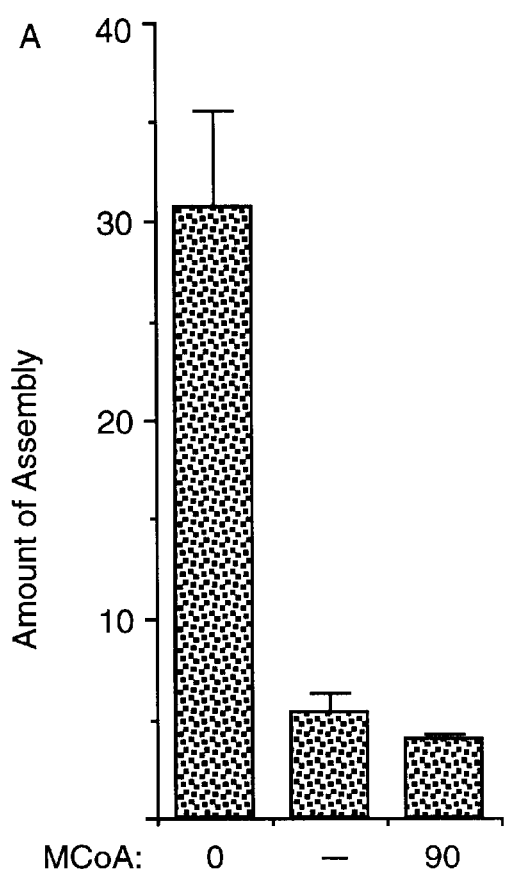
FIGS. 2A and 2B show the amount of capsid assembly occurring in a cell free system in the presence of MCoA added at different time points during the reaction (2A) and in the presence of two different concentrations of "NIKKOL"
Figure 2B:
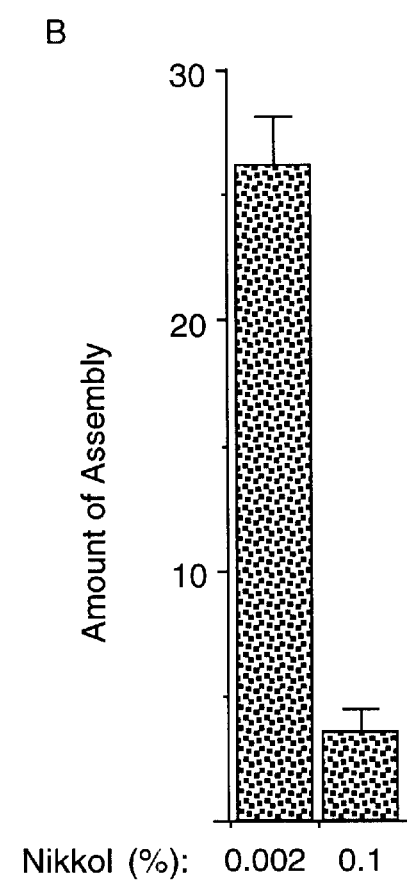

FIGS. 2A and 2B show the results of experiments carried out in support of the present invention in which the cell-free translation/assembly reaction was run in the absence or presence of certain components. FIG. 2A shows the effects of addition of myristoyl coenzyme A (MCoA) to a cell-free translation and assembly reaction programmed with Gag transcript. As shown, the reaction was run in the absence of added MCoA ("-"), or with 10 $\mu$M MCoA added either at the start of the reaction ("0") or at 90 minutes into the reaction when translation is completed ("90"). The detergent-treated products of the cell-free reactions were separated into soluble and particulate fractions by centrifugation on step gradients, and radiolabeled protein in each fraction was visualized by SDS-PAGE and AR as described above. The amount of radiolabeled Pr55 in the particulate fraction (which contains assembled capsids) was determined by densitometry of bands and is expressed as percent of total Gag protein synthesized. The presence of MCoA had no effect on the total amount of Pr55 synthesized; however, it did affect the amount of assembly into capsids, as shown. In the absence of MCoA, or when MCoA was not added until late in the reaction at a post-translational phase (90 min), very little assembly occurred. Values shown are the average of 3 independent experiments, and error bars indicate standard error.

Without ascribing to any particular underlying mechanistic theory, the foregoing results suggest that capsid assembly in the cell-free system requires co-translational myristoylation. This is consistent with an N-terminal modification of the protein which may be required for interaction of the assembly proteins with the inner aspect of a plasma membrane fraction that is required for assembly (Gheysen, et al., 1989; Bryant and Ratner, 1990; Wang and Barklis, 1993; Platt and Haffar, 1994; Spearman, et al., 1994; Hockley, et al., 1994; Bryant and Ratner, 1990; Jacobs, et al., 1989). Consistent with these data, in experiments carried out in support of the present invention, a Gag mutant that fails to become myristoylated (G$\Delta$A) is also incapable of assembly in the cell-free system (see FIG. 4B).

2. Detergent-sensitive Component

Studies carried out in support of the present invention have revealed that another critical component of the HIV capsid formation is sensitive to detergent concentrations above the critical micelle concentration (cmc). Membrane fragments are present in the exemplary wheat germ extracts used in experiments described herein, as evidenced by sensitivity of the reaction to addition of detergent at concentrations that solubilize membranes.

Solubilization of membranes can be effected by addition of the detergent "NIKKOL" (octa-ethyleneglycol mono n-dodecyl ether; Nikko Chemical Co., Tokyo, Japan) at a concentration of 0.1%. At this concentration, "NIKKOL", a relatively gentle non-ionic detergent, had no effect on Gag polypeptide synthesis. However, as shown in FIG. 2B, "NIKKOL" at this concentration largely abolished capsid assembly. In the experiments shown, cell free translation and assembly reactions containing 10 $\mu$M MCoA were programmed with Gag transcript. "NIKKOL" was added at the start the translation reaction to a final concentration of 0.002 or 0.1%, as indicated. At the end of the incubation, the reactions were analyzed for amount of assembly as described above in relation to FIG. 2A. Values shown are the average of 3 independent experiments, and error bars indicate standard error. This effect was not observed when "NIKKOL" was used at a concentration of 0.002%, which is below that required to disrupt lipid bilayers (Walter and Blobel, 1980).

In further experiments carried out in support of the invention, it was found that "NIKKOL" added after the completion of the 150 min. assembly reaction did not diminish the amount of assembly, even when added to a concentration of 1.0%. Thus, it appears that whereas the integrity of the completed capsid shell is not sensitive to "NIKKOL" (even at high concentrations), assembly of this structure is inhibited by concentrations of "NIKKOL" that are sufficient to solubilize membranes. Further, as described in more detail below, when the Pr55 translation/assembly reaction was treated with emetine and 0.1% "NIKKOL" during a post-translational phase 50 min. into the reaction, assembly was dramatically reduced.

The foregoing data are consistent with the idea that membranes are required for newly-synthesized and myristoylated Pr55 chains to be assembled efficiently into capsids in the cell-free system.

3. Incubation Conditions

In experiments carried out in support of the present invention, it was found that optimum assembly in the cell-free system requires incubation at 25° C. for at least 150 min, though it is appreciated that these conditions can be varied somewhat while still obtaining translation and assembly. Most Pr55 synthesis occurs during the first hour of this incubation; significant capsid formation does not take place until the final 90 min of the reaction. Thus, an aliquot of the reaction incubated for only 50 min contains approximately 60% of the full-length Pr55 chains that are present in an aliquot incubated for the standard 150 min. However, essentially none of the chains present at the 50 min time point have assembled into capsids, while at 150 min 25% have completed the assembly process (see FIG. 3A).

Based on these observations, it was possible to separate the translation and assembly phases of the reaction. To confirm this, a reaction mixture was split into two aliquots after 50 min incubation time. To one aliquot emetine was added. (Emetine blocks translation by inhibiting chain elongation.) Both aliquots were incubated to the 150 min. time point. While total Pr55 synthesis in the emetine-treated reaction was 60% of the control, the proportion of capsid assembly in this treated reaction was comparable to that of the untreated control (FIG. 3A, bar graph), indicating that assembly takes place even when translation is halted. These data provide basis for dividing the reaction into two phases, where manipulations performed after emetine treatment are observed to have effects on only the post-translational phase of assembly and should not affect Pr55 synthesis, which is already completed.

4. Energy Requirement

According to an important aspect of the invention, assembly of capsids is dependent upon the presence of an energy source in the reaction mixture. An exemplary energy source is the creatine phosphate-creatine phosphokinase system, which regenerates ATP. Equivalent energy sources will be known to those skilled in the art. In experiments carried out in support of the invention, cell-free translation and assembly reactions were programmed with Pr55 in the presence of 10 $\mu$M MCoA. Gag translation was allowed to proceed for 50 min, at which point further protein synthesis was inhibited by addition of 0.2 $\mu$M emetine. Immediately after emetine treatment, apyrase, an enzyme that hydrolyzes ATP, was added at a concentration of 1 unit/microliter to one of the emetine-treated reactions. At the end of the incubation (150 min), 1 $\mu$l of each reaction was analyzed directly by SDS PAGE (autoradiographs are shown below bar graph). The remainder of the products were analyzed for amount of assembly as described above. Shown in the bar graph is the amount of Pr55 assembled as a percent of total Pr55 synthesized in each reaction. Values in the bar graph are the average of 3 independent experiments, and error bars indicate the standard error.

Figure 3A:
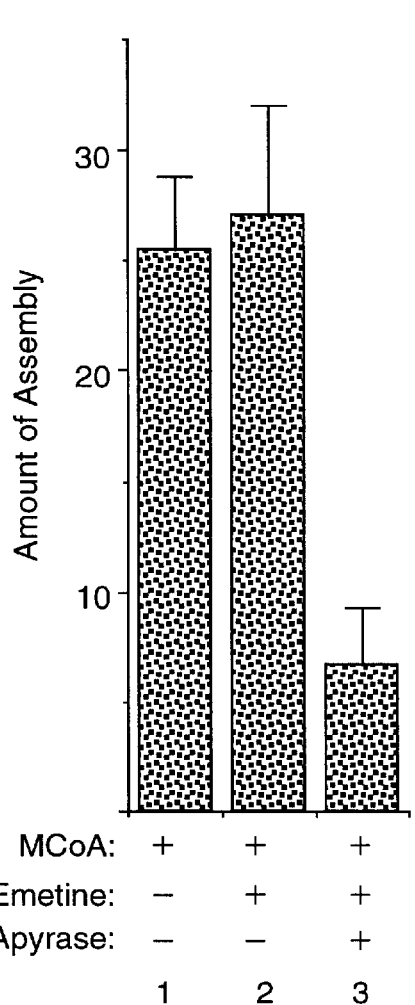
FIGS. 3A and 3B show bar graphs demonstrating the effect on assembly of inhibition of protein synthesis and depletion of ATP fifty minutes into the reaction (3A) and the requirement for a membrane fraction in the reaction (3B)

Depletion of free ATP from the assembly reaction by apyrase treatment resulted in a dramatic reduction in capsid assembly (FIG. 3A, bar graph). The effect of ATP depletion was not reversed by addition of the non-hydrolyzable analogue AMP-PNP after apyrase treatment, suggesting that ATP hydrolysis, and not just ATP binding, is required. Addition of apyrase did not change the total amount of Pr55 synthesis, as assessd by measurement of amount of protein by SDS-PAGE analysis, confirming that the effect was on capsid assembly rather than on protein translation. Furthermore, adding apyrase to the reaction after capsid assembly was completed had no effect on the amount of assembly, indicating that the ATP depletion did not affect capsid stability. These data indicate that there is a requirement for an energy source such as ATP in the capsid assembly process, and that this ATP dependence is distinct from the energy requirements of protein synthesis.

5. Detergent-insensitive Subcellular Component

According to another feature of the invention, it was found that reconstitution of the reaction mixture with a subcellular fraction promotes assembly. As described below this component is distinguished by its relative insensitivity to detergent. Specifically, it is not inactivated by exposure to 0.5% "NIKKOL".

Wheat germ extract was subjected to ultracentrifugation as described in Example 2 to generate the high speed supernatant (HSS, depleted of components having sedimentation velocities of 90S or greater), high speed pellet (HSP), and detergent-treated high speed pellet (HSPd). The HSS was used to program cell-free translation and assembly reactions in the presence or absence of 10 $\mu$M MCoA (as indicated in FIG. 4B). Each of these reactions was treated with the protein synthesis inhibitor emetine at 50 min. Following this, the HSP or HSPd was added to aliquots of the reaction as indicated below the bar graph in FIG. 3B. All reactions were incubated for a total of 150 min. A 1 microliter aliquot was removed and analyzed directly by SDS PAGE (shown below bar graph in FIG. 3B). The remainder of each reaction was analyzed for amount of assembly as described above and plotted as percent of total Pr55 present in each reaction. The values shown in the bar graph are the average of 3 independent experiments, and error bars indicate the standard error.

Figure 3B:
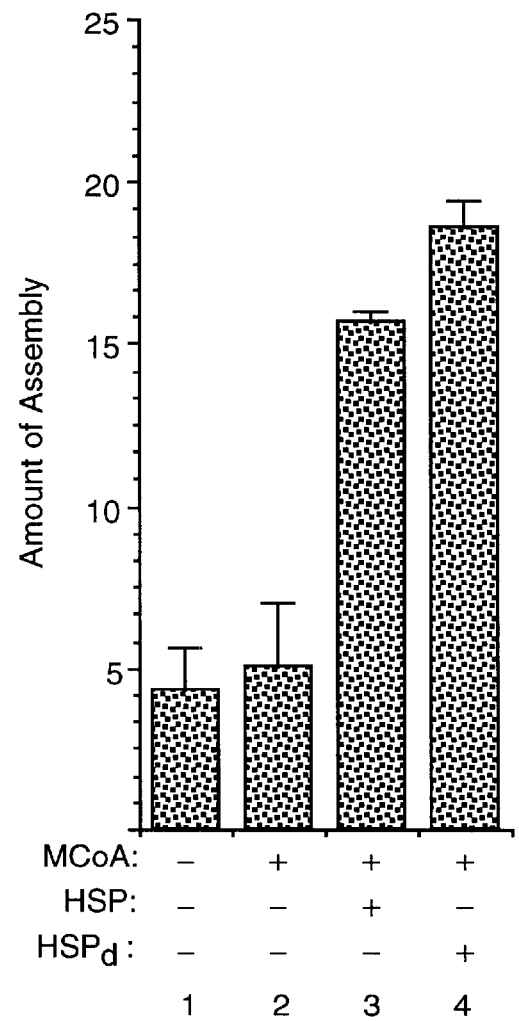

These experiments showed that the HSS, depleted of components that were 90-S or greater, supported Pr55 translation but not its assembly (FIG. 3B). This indicates that the HSP likely contains assembly-specific host factor(s). This was demonstrated directly by showing that addition of the HSP post-translationally (following emetine treatment) to unassembled Gag chains synthesized in the HSS resulted in a considerable restoration of particle assembly (FIG. 3B). In these experiments, total synthesis of Pr55 was unaltered by addition of the HSP. Together, these data indicate that a subcellular fraction of the eukaryotic cell lysate is required for post-translational events in capsid assembly to take place. That this component is distinct from the plasma membrane component described above is evidenced by the experiments described below indicating that, unlike the plasma membrane component, this component is not sensitive to treatment with a non-ionic detergent.

HSP was examined for the presence of a detergent-sensitive component that is required for capsid formation. HSP was prepared from a cell extract treated with detergent (0.5% "NIKKOL"). The resulting HSP ("HSPd") was washed with detergent-free buffer, and was added post-translationally to an assembly reaction. As shown in FIG. 3B, HSP from the detergent-treated extract was equally as active in promoting post-translational capsid formation as the control HSP (FIG. 3B, bar graph). The separate detergent-sensitive and detergent-insensitive host factors appear to be involved in the post-translational phase of HIV capsid assembly. Furthermore, the detergent-insensitive host factor can be depleted by ultracentrifugation and then reconstituted by post-translational addition. According to a further feature of the invention it is appreciated that the detergent-insensitive subcellular component can be further fractionated and characterized.

1. Capsid Assembly Intermediates

According to an important aspect of the present invention, the cell-free capsid assembly system identified herein reveals the existence of novel previously unrecognized assembly intermediates, and provides means for identification of additional assembly intermediates. As discussed in more detail below, such intermediates are useful as (i) antigens for production of antibodies and/or vaccines, (ii) along with such antibodies, as standards in diagnostic tests, and (iii) as vehicles for identification of key host cellular proteins involved in capsid assembly.

Exemplified herein are a capsid assembly pathway and intermediates thereof that have been identified for HIV. According to a further feature of the present invention, it is appreciated that similar pathways are used by other retroviral capsid assembly mechanisms. Furthermore, it is appreciated that the intermediate described herein have analogous counterparts in such retroviral systems. These counterparts are identified using the general manipulations described below with respect to HIV.

As is described in the sections that follow the capsid assembly, intermediates can be formed in a number of ways, including but not limited to (i) translation of HIV capsid assembly mutant coding sequences in cells or in cell-free preparation, and (ii) by blocking the production of HIV capsids in a cell-free assembly system, such as by adding specific assembly blockers or by subtracting of a key component, such as MCoA, from the reaction, resulting in the production of one or more assembly intermediates in large quantity.

1. HIV Mutant Capsid Formation

Studies of capsid assembly in cultured cells have revealed that certain mutations within the Gag coding region disrupt immature HIV capsid assembly. Four previously-described mutations in Gag are diagrammed in FIG. 4A: i) the Pr46 mutant, in which the C terminal p6 domain of Gag is deleted (Jowett, et al., 1992; Spearman, et al., 1994; Royer, et al., 1991; Hockley, et al., 1994); ii) the Pr41 mutant, in which the deleted domains include p6, the entire nucleocapsid region (p7), and the distal end of p24 containing the p24-p7 protease cleavage site (Gheysen, et al., 1989; Jowett, et al., 1992; Hockley, et al., 1994); iii) the D2 mutation, in which 10 amino acids of the p24 domain of Gag (upstream of the p24-p7 protease cleavage site) are deleted (Zhao, et al., 1994; Hockley, et al., 1994); and iv) the GΔA mutation, an N-terminal single amino-acid substitution that abolishes myristoylation of Gag (Gottlinger, et al., 1989; Bryant and Ratner, 1990). Upon expression in cells, only the Pr46 mutant was capable of producing viral particles indistinguishable from those produced by expression of wild-type Gag (Jowett, et al., 1992; Spearman, et al., 1994; Royer, et al., 1991; Hockley, et al., 1994). Each of the other three mutations fails to result in efficient viral particle production and release (Gheysen, et al., 1989; Jowett, et al., 1992; Hockley, et al., 1994; Zhao, et al., 1994; Gottlinger, et al., 1989; Bryant and Ratner, 1990).

Figure 4A:
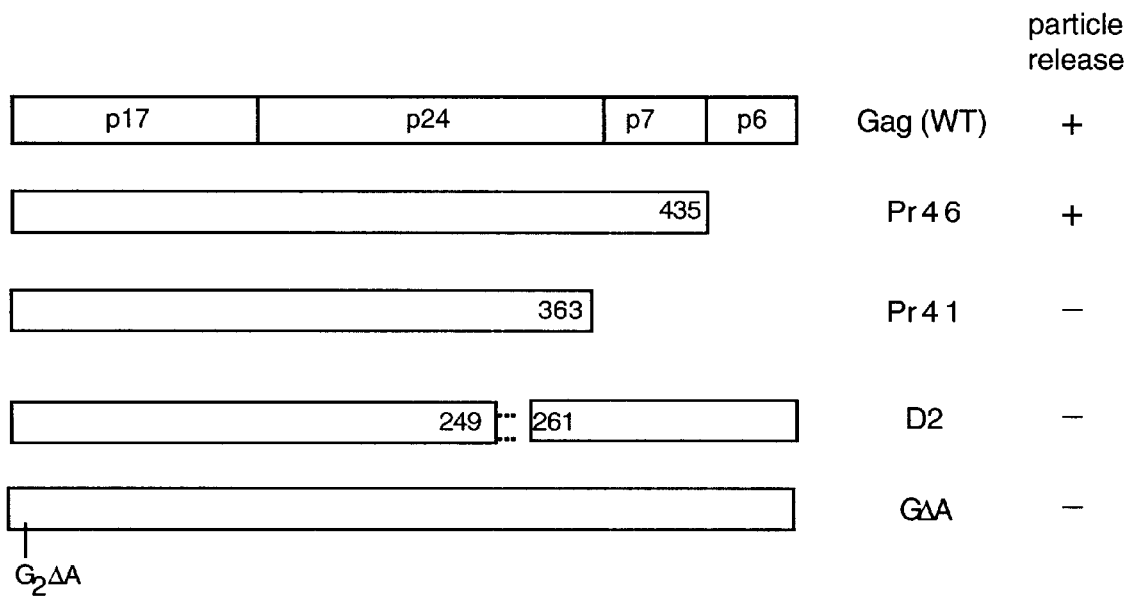
FIGS. 4A and 4B show schematic diagrams of mutations within Gag (4A), and the amount (4B) of capsid assembly that occurred in the cell-free system primed with transcripts of the various mutant HIV viruses shown in FIG. 4A, as well as wild-type capsids (WT) and capsids produced in the absence of MCoA (-MCoA)
Figure 4B:
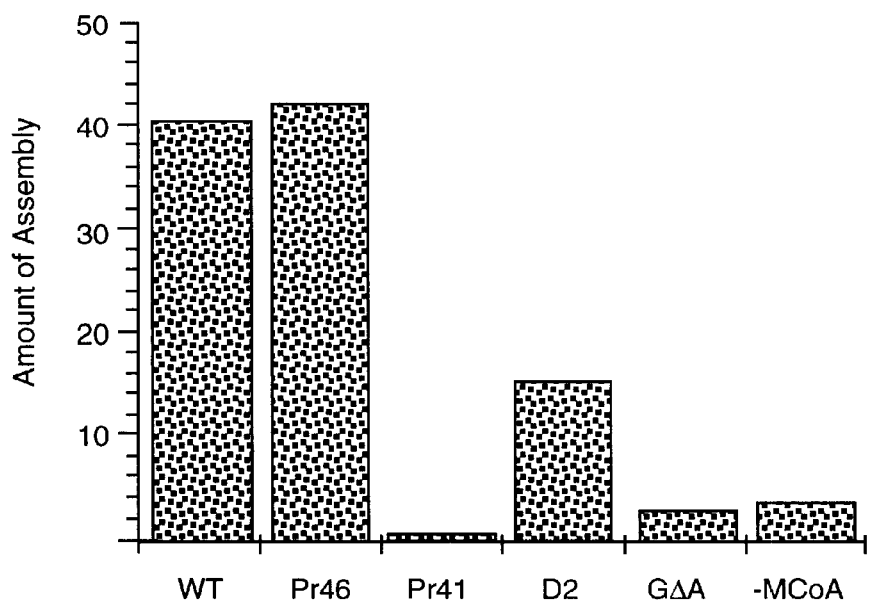

FIG. 4A shows schematically the Gag polyprotein precursor that consists of four domains, referred to as p17, p 24, p7, and p6, and the mutants discussed above. The Pr46 and Pr41 mutants were constructed by introducing a stop codon truncation at amino acid 435 or at amino acid 363, respectively. In the D2 mutation, amino acids 249 to 261 are deleted. In the GΔA mutation, the glycine at amino acid 2 is substituted with an alanine, thereby blocking myristoylation. The known phenotypes with respect to particle release from cells expressing each of these mutants is indicated to the right (for references, see text).

FIG. 4B shows capsid assembly in cell-free reactions programmed with Gag mutants. Cell-free translation and assembly reactions were programmed with transcript coding for each of the Gag mutants described above, as well as transcript coding for wild-type Gag in the presence or absence of MCoA (labeled WT and -MCoA, respectively). At the end of the reaction period, each sample was detergent treated, fractionated on velocity sedimentation on 13 ml sucrose gradients, and analyzed by SDS-PAGE and autoradiography. The amount of radiolabeled translation product in the position of completed 750-S capsids was quantitated by densitometry and expressed for each reaction as % of total synthesis. The total amount of translation was approximately equal in all reactions.

As is shown in FIG. 4B, the Pr41 and GΔA mutants failed to assemble completed capsids, while approximately 40% of the total translation product of both wild-type Gag and the assembly-competent Pr46 mutant assembled into completed capsids. The non-assembling D2 mutant appeared to have generated a small amount of material in the region of completed capsids, but further analysis of this material revealed it to be the trail of a large Gag complex (of approximately 400–500 S) that does not comigrate with completed capsids (see FIG. 6E). Thus, like Pr41 and GDA, D2 did not assemble into the 750-S completed capsid. Together, these data indicate that the cell-free system appears to reproduce phenotypes of a variety of assembly-defective and assembly-competent mutations in Gag.

2. Identification of HIV Capsid Intermediates

The requirement for host factors and ATP suggests that discrete biochemical intermediates exist during the assembly process. Heretofore, such intermediates in HIV capsid assembly have not been described. However, according to a further aspect of the present invention, it is appreciated that the cell-free system of the present invention constitutes a good system for detecting assembly intermediates.

Figure 5A:
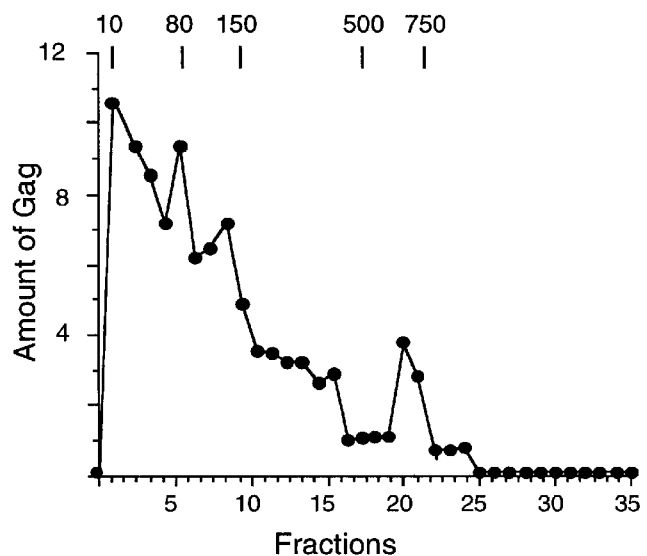
FIGS. 5 (A–C) show pulse-chase analysis of HIV capsid assembly by velocity sedimentation in a continuously labeled cell-free reaction mixture (5A) where the calculated positions of 10-S, 80-S, 150-S, 500-S, and 750-S complexes are indicated by markers at the top of the graph, and in reactions to which unlabeled $^{35}$S cysteine was added 4 minutes into the reaction and aliquots were taken for sedimentation analysis after 25 minutes (5B) and 15 minutes of reaction (5 C), and samples were further analyzed by SDS gel and radiography.

In experiments carried out in support of the present invention, a continuously-labeled cell-free reaction was analyzed by velocity sedimentation. Cell-free translation and assembly of Pr55 was performed as described above. Upon completion of the cell-free reaction, the products were diluted into 1% NP40 sample buffer on ice, and were analyzed by velocity sedimentation on 13 ml 15–60% sucrose gradients. Fractions were collected from the top of each gradient, and the amount of radiolabeled Pr55 protein in each fraction was determined and expressed as percent of total Pr55 protein present in the reaction. The calculated positions of 10-S, 80-S, 150-S, 500-S, and 750-S complexes are indicated with markers above the figures (cf., FIG. 5A). 750-S represents the position of authentic immature (de-enveloped) HIV capsids. The intermediate complexes having calculated sedimentation coefficients of 10-S, 80-S, 150-S and 500-S are referred to herein as intermediates A, B, C and D, respectively.

Figure 5B:
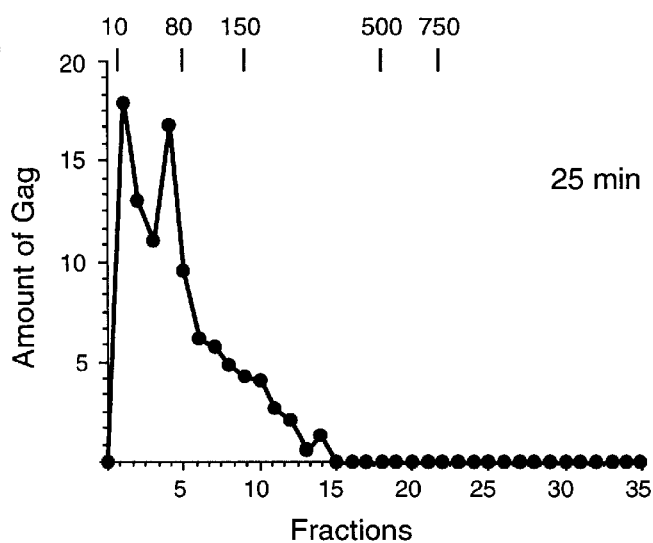
Figure 5C:
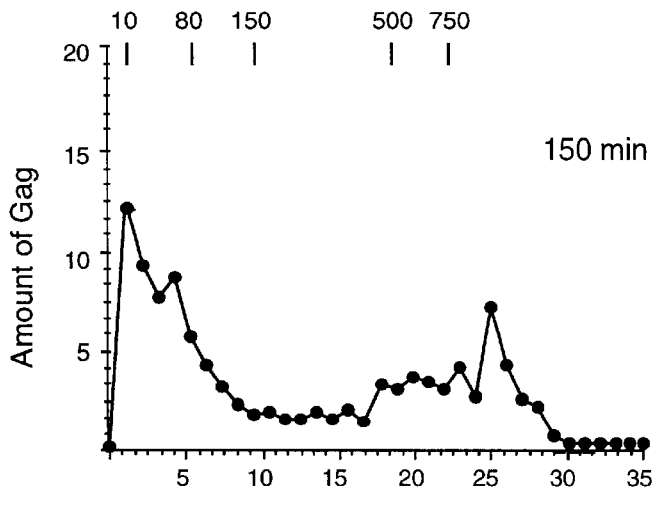
Figure 7A:
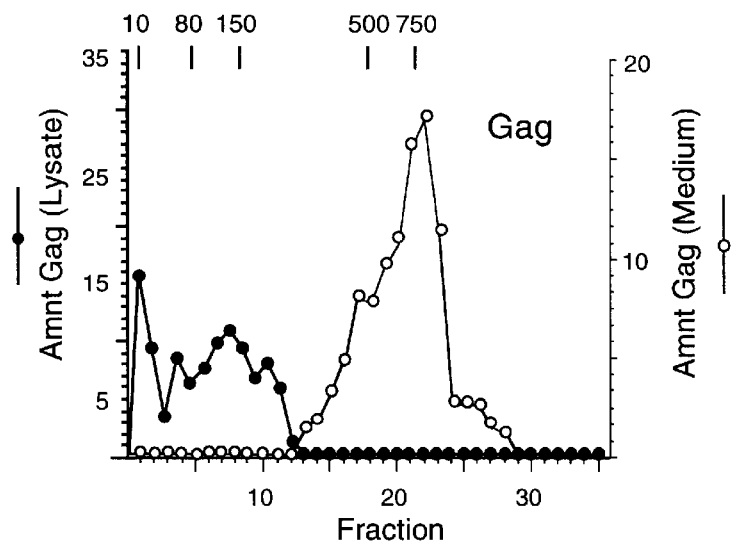
FIGS. 7(A–C) show plots of sedimentation of Gag complexes isolated from COS-1 cells transfected with a transfection vector encoding Pr55 cDNA wild-type Gag (7A) or by transfection vectors encoding the p41 mutant (7B) or the D2 mutant (7C)
Figure 7B:
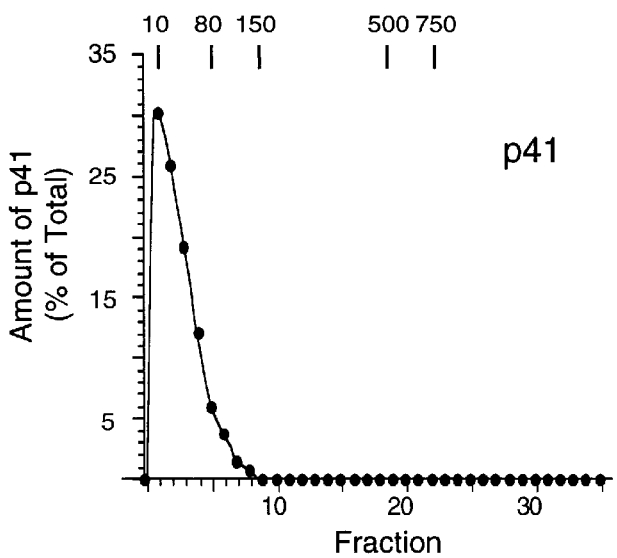
Figure 7C:
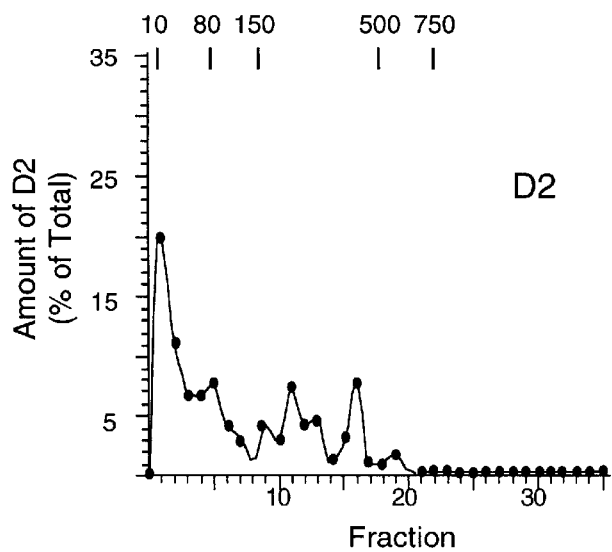

Further experiments in support of the present invention indicate that the identified intermediates represent assembly intermediates, as evidenced by the observation that they are present in large quantities at early time points, and are diminished at later times during the reaction. Specifically, pulse-chase analysis was used to follow a small cohort of radiolabeled Pr55 chains over time during the assembly reaction. Cell-free translation and assembly of Pr55 was performed according to the methods set forth in Example 1, except that $^{35}S$ cysteine was used for radiolabeling. At 4 min into the translation reaction, an excess of unlabeled cysteine was added to the reaction so that no further radiolabeling would occur. Aliquots of the reaction were collected 25 min (FIG. 5C) and 150 min (FIG. 5D) into the reaction. One microliter of each aliquot was analyzed by SDS-PAGE and AR to reveal the total amount of radiolabeled Pr55 translation product (indicated by arrow in FIG. 5B) present at each chase time. The remainder of the aliquots were diluted into 1% NP40 sample buffer on ice, and were analyzed by velocity sedimentation on 13 ml 15–60% sucrose gradients (FIGS. 5C and 5D respectively), in the manner described for FIG. 5A above.

The total amount of radiolabeled Pr55 was the same at 25 min and 150 min into the pulse-chase reaction, indicating that neither further radiolabeling nor degradation of Pr55 chains occurred after 25 min, and confirming that the same population of Pr55 chains was being analyzed at both times.

After 25 minutes of reaction time, all of the radiolabeled Pr55 was found in complexes A, B, and C (FIG. 5C), with no radiolabeled Pr55 chains present in the region of completed 750-S capsids. While complexes A and B appear as peaks at approximately the 10-S and 80-S positions of the gradient, complex C appears as a less distinct shoulder in approximately the 150-S position. In marked contrast, examination of the assembly reaction at 150 minutes showed that a significant amount of radiolabeled Pr55 was assembled into completed capsids that migrated in the 750-S position (FIG. 5D). Correspondingly, the amount of Pr55 in complexes A, B, and C was diminished by precisely the amount that was now found to be assembled, demonstrating that at least some of the material in complexes A, B, and C constitutes intermediates in the biogenesis of completed 750-S capsids.

At extremely short chase times (i.e., 13 min), when only some of the radiolabeled chains have completed synthesis, full length Pr55 chains were found exclusively in complex A on 13 ml sucrose gradients, while nascent chains that are not yet completed were in the form of polysomes of greater than 100-S. Thus, polysome-associated nascent chains of Gag constitute the starting material in this pathway, and the 10-S complex A, which contains completed Gag chains, is likely to be the first intermediate in the formation of immature capsids. Therefore, complexes B and C may represent later assembly intermediates in the pathway of capsid formation.

As further confirmation that complexes A, B, and C constitute intermediates in HIV capsid assembly, it is shown below that blockade of assembly results in accumulation of Gag chains in the form of complexes with S values corresponding to the S values of A, B and C. Additional evidence is provided by data showing that blockade at different points along the pathway results in accumulation of complexes A, B, and C in various combinations, as determined by the order of their appearance during the course of assembly. For example, if an ordered pathway of intermediates exists, then blockade at early points in the pathway should result in accumulation of one or two Gag-containing complexes corresponding to early putative assembly intermediates, while blockade at a very late point in the pathway would result in accumulation of all the putative assembly intermediates but not the final completed capsid product.

a. Pharmacological Blockade of Assembly. Capsid assembly was disrupted by adding either apyrase post-translationally (as described in Section II.C.4) or detergent co-translationally (as described in Section II.C.2), and the reaction products were analyzed by velocity sedimentation. Material in fractions corresponding to the assembly intermediates and completed capsid were quantified and are presented in Table 1.

TABLE 1

|  | A | B/C | Final Capsid |
| --- | --- | --- | --- |
| untreated | 2798 | 5046 | 739 |
| + apyrase | 2851 | 5999 | 133 |
| + detergent | 2656 | 6130 | 189 |

The untreated reaction contained Pr55 in complexes A, B, and C, as well as a peak in the final 750-S capsid position, while the treated reactions contained no peak at the position of the final capsid product (Table 1). Treatment with either apyrase or detergent resulted in accumulation of additional material in complexes B and C, but did not result in accumulation of additional material in complex A. This is consistent with the idea that complexes B and C are the more immediate precursors of the 750-S completed capsids, and that these interventions block the conversion of complexes B and C into the fully-assembled capsid end-product.

b. Assembly-Defective Mutants. Further evidence of the existence of assembly intermediates A, B and C comes from experiments carried out in support of the present invention in which the intermediates accumulated when capsid assembly was blocked by specific mutations in Gag. Cell-free reactions were programmed with each of the previously-described assembly-competent and assembly-defective Gag mutants (see FIG. 4), and were incubated for 150 min. The reaction products were diluted into 1% NP40 sample buffer on ice, and were analyzed by velocity sedimentation on 13 ml 15–60% sucrose gradients then analyzed by velocity sedimentation. Reactions programmed with wild-type Gag (FIG. 6A) or the assembly-competent Pr46 mutant (FIG. 6B) were found to have nearly identical profiles, in which over 30% of the radiolabeled chains synthesized formed completed immature capsids (that migrate at 750-S) and the remainder was in the form of residual putative assembly intermediates A and B. Thus, these two assembly-competent forms of Gag appear to be equally efficient at capsid assembly in the cell-free system.

FIG. 6C shows the same analysis for the assembly-defective Pr41 mutant. All radiolabeled chains at the end of the Pr41 cell-free reaction were contained in a single, approximately 10-S complex, corresponding to complex A. Since the 10-S peak was very large and led to an irregular trail that could be masking 80-S or 150-S peaks, products of the Pr41 reaction were re-analyzed on a gradient that allowed high resolution in the 1 to 200-S size range. All of the Pr41 translation product was in fact present in complex A, which was approximately 10-S in size. Thus, in the cell-free system, it appears that Pr41 fails to progress beyond complex A, which is likely to represent the first intermediate in the assembly pathway.

Like Pr41, the myristoylation-incompetent GΔA mutant failed to assemble into 750-S capsids (FIG. 4B, FIG. 6D), but unlike Pr41, GΔA had distinct peaks in both the 10-S and 80-S regions of the gradient (compare FIG. 6D to FIG. 6C). These data indicate that the GΔA mutant, which contains the entire Gag coding region except for the myristoylation signal, is capable of forming complex A, which appeared to be the first assembly intermediate in the pulse-chase experiment, as well as complex B, but does not progress further towards forming completed capsids. These data suggest that complex B is likely to be the second assembly-intermediate formed in the biogenesis of immature HIV capsids.

As shown above, in the absence of exogenously-added MCoA, wild-type Gag failed to assemble in the cell-free system (FIG. 2A), consistent with previous observations that myristoylation is required for proper capsid assembly to occur. Thus, a cell-free reaction programmed with wild-type Gag but performed in the absence of MCoA would be expected to be blocked at the same point in the assembly pathway as the GΔA mutant. Consistent with this, experiments carried out in support of the present invention demonstrate that assembly performed in the absence of MCoA results in formation of only complexes A and B and therefore closely resembles the GΔA mutant shown in FIG. 6D.

Analysis of a cell-free reaction programmed with the D2 mutant is shown in FIG. 6E. Unlike the previously described assembly-defective mutants, D2 was found to form a spectrum of Gag-containing complexes, including peaks corresponding to complexes A and B (at approximately 10-S and 80-S), a shoulder corresponding to complex C (in the 150-S region), and an additional peak of approximately 400–500-S, that will henceforth be referred to as complex D. Note that complex D trails into the 750-S region, accounting for the appearance of small amount of assembly in the simpler analysis of capsid formation presented in FIG. 1. However, the detailed analysis presented here makes it clear that in fact there is no discrete peak in the region of completed capsid (750-S). Thus, the D2 mutant appears to form a series of complexes corresponding in size to the assembly intermediates seen in the pulse-chase experiment (FIG. 6), as well as an additional complex of larger size, but fails to produce the completed 750-S product.

3. Host Cell Proteins Involved in Capsid Intermediate Formation

In further experiments carried out in support of the present invention, capsid intermediates formed and isolated as described above were analyzed for the presence of additional protein species. Immunoprecipitation reactions were carried out using several antibodies directed to cellular proteins. Surprisingly, a monoclonal antibody which recognizes a molecular chaperone known as TCP-1, antibody "23c", was found to specifically interact with capsid intermediate fractions. TCP-1 is a 55–60 kD polypeptide that resides in a 20S particle and is not known to play a role in viral capsid assembly. Interestingly, antibody 23c does not recognize the human or yeast homologs of TCP-1, but it does recognize a number of other eukaryotic proteins, presumably through recognition of their common C-terminal epitopes (LDD-COOH).

Further experiments in support of the invention revealed that the 23 c reactive protein present in wheat germ extract migrates on SDS polyacrylamide gels as a 68 kilodalton protein. This protein is referred to herein as host protein 68 (HP 68). Further analysis reveals that the protein includes a peptide region having the following sequence: PRPYLD-VKQRLKAARVIRSLLRSN (SEQ ID NO: 2).

Association of HP 68 with the previously identified capsid assembly intermediates was assessed by measuring immunoreactivity of the 23c antibody. FIG. 10 shows the distribution of inimunoreactivity of 23c antibody with various intermediates. In these experiments, cell-free capsid formation reactions were programmed with Gag transcript (Example 1), pulse-labeled with 35-S cysteine for 3 minutes, and then chased with an excess of unlabeled cysteine. Under these conditions, chains synthesized during the first 25 minutes of the reaction are radiolabeled, while subsequently formed chains are unlabeled. Aliquots of the cell-free reaction were removed at various times during incubation and were either analyzed directly by SDS-PAGE or were subjected to immunoprecipitation with 23c antibody (Example 4).

In these reactions, it was verified that the total number of radiolabeled chains synthesized over time remained relatively constant, while the number of radiolabled chains in the form of fully assembled capsids increased progressively over the course of reaction, from 1.0% to 50.0%, with the largest increase in completed capsids occurring after 75 minutes. In contrast, the number of radiolabeled Gag chains bound to HP 68 (as assessed by immunoprecipitation with 23c) was very low just after synthesis was completed, but increased significantly over time, reaching a peak at approximately 75 minutes into the incubation, then decreasing substantially during the final hour of the cell-free reaction. These observations are consistent with the conclusion, illustrated below, that HP 68 does not bind specifically to either newly-synthsized, unassembled Gag chains or to fully-assembled capsids.

In further experiments, radioactive HIV assembly intermediates formed as described above were subjected to velocity sedimentation, followed by immunoprecipitation using the 23c antibody. With reference to the schematic shown in FIG. 8A, radiolabeled Gag chains in the form of the 80S and 500S assembly intermediates (intermediates B and D, respectively) were immunoreactive with 23c antibody, while fully assembled 750S capsids were not immunoreactive. Although intermediate C (150S) showed little or no immunoreactivity in these experiments, there is also very little of this intermediate present in the mixture at the time point assayed (2 hours), so the presence of HP 68 in this fraction cannot be ruled out.

These results were also confirmed using assembly incompetent mutant viruses, as discussed above. Table 2 shows the results of experiments in which various assembly incompetent mutants or reaction manipulations were used to assess HP 68 association with the above-defined intermediates. Cell-free reactions were programmed with wild-type ("Gag"), mutants Pr46 ("p46"), GΔA or Pr 41 ("p41"), or were carried out in the presence of detergent ("Gag+det") or with the addition of apyrase ("Gag+apy"). Distribution of the above-described intermediates A-D and completed capsids was assessed for each condition, as described above, and 23c immunoreactivity was determined.

TABLE 2

Distribution of Gag-containing Intermediates

|  | A | B | C | D | complete capsid | 23c immunoreactivity |
|---|---|---|---|---|---|---|
| Gag | + | ++ | + | ++ | +++ | ++ |
| p46 | + | ++ | + | ++ | +++ | ++ |
| Gag + det | ++ | ++ | + | − | − | + |
| Gag + apy | ++ | ++ | + | − | − | + |

TABLE 2-continued

Distribution of Gag-containing Intermediates

|  | A | B | C | D | complete capsid | 23c immunoreactivity |
|---|---|---|---|---|---|---|
| GΔA | ++ | ++ | − | − | − | + |
| p41 | +++ | − | − | − | − | − |

As illustrated, the absence of 23c immunoreactivity in the Pr41 mutant reaction, which fails to form any high molecular weight intermediates, indicates that there is no association of HP 68 with intermediate A; in contrast, wild-type Gag and Pr46 mutant, which form high intermediates B–D are highly reactive. In the presence of detergent or apyrase, assembly intermediates A–C accumulate, as described above; under these conditions, 23c immunoreactivity was observed.

The foregoing data support one of the discoveries of the present invention—that assembly of HIV capsids involves a host protein derived from the host cell, exemplified herein by HP 68. In accordance with the present invention, HP 68 is (i) is immunoreactive with monoclonal antibody 23c, and (ii) includes the sequence SEQ ID NO: 2. The present invention also appreciates that other cellular homologs of HP 68 perform a similar function in hosting HIV assembly. Specifically contemplated by the present invention is a human homolog of HP 68 which is associated with intermediates B–D present in human cell systems. By "homolog" is meant a protein or proteins that resemble HP 68 in sequence (at least about 75% sequence identity by a standard protein/nucleotide sequence comparison algorithm), and which can be isolated from or detected in association with HIV capsid intermediates B–D.

4. Correspondence of Cell-free Capsid Intermediates to Cell-produced Capsid Intermediates Cos-1 cells were transfected with a transfection vector encoding Pr55 cDNA, as described in the Examples. Four days later, the medium from the cells was collected. Viral particles in the medium were harvested by ultracentrifugation through a 20% sucrose cushion and then treated with detergent to remove envelopes. The transfected cells were solubilized in detergent to generate the cell lysate. The particles from the medium (FIG. 6A, right ordinate, open circles) and the detergent lysate of the cells (FIG. 6A, left ordinate, closed circles) were analyzed in parallel by velocity sedimentation on 13 ml 15–60% sucrose gradients. The amount of Pr55 protein in each fraction of these gradients was determined by immunoblotting and is expressed as percent of total Pr55 protein present. The calculated positions of 10-S, 80-S,150-S, 500-S, and 750-S complexes are indicated with markers above each graph. 750-S represents the position of authentic immature (de-enveloped) HIV capsids.

Different cultures of Cos-1 cells were transfected with a transfection vector encoding the Pr41 mutant (FIG. 6B) or the D2 mutant (FIG. 6C). Transfected cells were lysed in detergent, and the lysate was analyzed by velocity sedimentation on 13 ml sucrose gradients, as in the experiments described with reference to FIG. 8A, above. The amount of capsid protein in each fraction of these gradients was determined by immunoblotting with anti-Gag antibody, and was expressed as percent of total immunoreactive protein present in each reaction. As shown, a substantial amount of fully-assembled 750-S capsid was present in the medium (FIG. 6A, open circles), while the cell lysate contained no 750-S capsids (FIG. 6A, closed circles). These data are consistent with correspondence of intermediates in vivo with those reported above for cell-free capsid synthesis and assembly.

Analysis of the Pr41 mutant transcript is shown in FIG. 6B. This mutant appears to be blocked after the first assembly intermediate in the cell-free system. Analysis of the D2 mutant, which appears to be blocked at the end of the assembly pathway in the cell-free system, shows accumulation of corresponding Gag-containing complexes within cells. Cos cells were transfected with each of these mutants, and the medium as well as the lysate were examined by immunoblotting. Medium from cells transfected with the assembly-defective Pr41 or D2 mutants did not contain 750-S completed capsids. The cell lysate of Cos cells transfected with the Pr41 mutant contained only material that peaked in the 10-S region of the velocity gradient (FIG. 6B), resembling what had been found when the Pr41 mutant was expressed in the cell-free system (see FIG. 5C). The observation that the Pr41 reaction product migrated as a single complex that peaked in the 10-S region was confirmed by analysis on a variety of different velocity sedimentation gradients that allowed higher resolution in the 1 to 200-S size range.

In contrast, the cell lysate of Cos cells transfected with the D2 mutant contained a spectrum of immunoreactive complexes that ranged in size from 10-S to 500-S (FIG. 6C), resembling what was found when D2 was expressed in the cell-free system (FIG. 5E). Thus, the data from transfected cells suggests that the behavior of Gag mutants in the cell-free system reflects events in capsid assembly that occur in living cells.

4. Model for Capsid Assembly

A model of the HIV capsid assembly pathway is shown in FIG. 8A. This model is based on the simplest interpretation of the data presented herein. This model is presented for purposes of summarizing these data, and is not to be construed as a representation of a particular underlying mechanism to which the present invention must adhere. In particular, the exact relationship of the subcellular fraction dependent step, as well as the apyrase- and detergent-sensitive steps to the pathway are not to be taken as a basis for limiting the claimed method or cell-free system of the present invention. Moreover, although the order of complex formation shown is consistent with the data presented, this order should not be used to limit the claimed intermediate compositions.

According to the model presented in FIG. 8A, newly-synthesized Gag proteins are myristoylated co-translationally. Nascent Gag polypeptides appear to chase into completed immature capsids by way of a series of Gag-containing complexes (complexes A, B, C, and D). Evidence from the studies reported herein suggests that complexes A, B, and C may constitute assembly intermediates. Complex D may similarly constitute an assembly intermediate or may represent a side-reaction. A subcellular, detergent-resistant factor appears to be required for capsid formation. In addition, ATP and a membrane fraction are also required for assembly to take place, as evidenced by apyrase and detergent sensitivity of the assembly process.

FIGS. 8(B–D) show the proposed correspondence between assembly mutants p41, GΔA, D2 and p46 to the model pathway, based on the data presented above.

IV. Utility

The methods and compositions described herein have a number of useful purposes. For example, the cell-free translation/assembly system for HIV can be used to produce large quantities of the wild-type capsids, capsid intermediates or mutant capsids, as demonstrated in the studies described herein. Such capsids and intermediates can be used, for example to produce vaccines. They also find utility as reagents in screening assays that assess the status of HIV capsid formation or in assays used for screening for drugs that interfere with HIV capsid formation, such as the assay described below.

The screening assay of the invention has utility in screening for new drugs for use in the attenuation of HIV infection. The assay can be set up according to any of a number of assay formats. In one such assay, cell-free translation and assembly is carried out (in the presence or absence of a candidate drug) in a liquid phase, along the lines of the assay described in Example 1. The reaction product is then added to a solid phase immunocapture site coated with antibodies directed against and specific for one or more of the HIV capsid intermediates or the complete HIV capsid described above. In this way, the precise point of assembly interference of the drug can be determined. Such information should be valuable to clinicians, and drug development companies, particularly in the context of combination therapeutics against HIV infection.

Host cell proteins, exemplified by HP 68, also form a part of the present invention, and have distinctive utilities. For example, such proteins, or specific antibodies directed to such proteins, can be used to monitor capsid formation in the assays described above. In addition, association of the host protein with specific intermediates can be assayed directly, and such an assay can form a screening assay for drugs that interfere with capsid assembly by interfering with such association.

The following examples illustrate, but in no way are intended to limit the present invention.

MATERIALS

1. Chemicals

Chemical sources are as follows, unless otherwise indicated below: Nonidet P40 (NP40) was obtained from Sigma Chemical Co. (St. Louis, Mo.). "NIKKOL" was obtained from Nikko Chemicals Ltd. (Tokyo, Japan). Wheat Germ was obtained from General Mills (Vallejo, Calif.). Myristoyl Coenzyme A (MCoA) was obtained from Sigma Chemical Co. (St. Louis, Mo.).

2. Plasmid Constructions

All plasmid constructions for cell-free transcription were made using polymerase chain reactions (PCR) and other standard nucleic acid techniques (Sambrook, et al., 1989). Plasmid vectors were derived from SP64 (Promega) into which the 5' untranslated region of Xenopus globin had been inserted at the Hind III site (Melton, et al., 1984). The gag open reading frame (ORF) from HIV genomic DNA (a kind gift of Jay Levy; University of California, San Francisco) was introduced downstream from the SP6 promoter and the globin untranslated region. The GΔA mutation was made by changing glycine at position 2 of Gag to alanine using PCR (Gottlinger, et al., 1989). The Pr46 mutant was made by introducing a stop codon after gly 435 (removes p6); Pr41 has a stop codon after arg 361 (in the C terminal region of p24). These truncation mutants are comparable to those described by Jowett, et al., 1994, incorporated herein by reference. To make the D2 mutant amino acids from gly 250 to val 260 were deleted (as in Hockley, et al., 1994; Zhao, et al., 1994). All changes engineered by PCR were verified by DNA sequencing.

3. 35-S Energy Mix

35-S Energy Mix (5×stock) contains 5 mM ATP (Boehringer Mannheim), 5 mM GTP (Boehringer Mannheim), 60 mM Creatine Phosphate (Boehringer Mannheim), 19 amino acid mix minus methionine (each amino acid except methionine; each is at 0.2 mM), 35-S methionine 1 mCurie (ICN) in a volume of 200 microliters at a pH of 7.6 with 2 M Tris base.

4. Compensating Buffer

The Compensating Buffer (10×) contains 40 mM HEPES-KOH, at a pH of 7.6 (U.S. Biochemicals), 1.2 M KAcetate (Sigma Chemical Co.), and 2 mM EDTA (Mallinckrodt Chemicals, Paris, Ky.).

EXAMPLES

Example 1

Cell Free Protein Synthesis

1. Transcription

The plasmid containing the Gag coding region was linearized at the EcoR1 site (as described in the NEB catalogue). The linearized plasmid was purified by phenol-chloroform extraction (as described in Sambrook, et al., 1989) and this plasmid was adjusted to a DNA concentration of 2.0 mg/ml. The transcription was carried out using a reaction that contained: 40 mM Tris Ac (7.5), 6 mM Mg Ac, 2 mM Spermidine, 0.5 mM ATP, 0.5 mM CTP, 0.5 mM UTP, 0.1 mM GTP, 0.5 mM diguanosine triphosphate (cap), 10 mM Dithiothreitol, 0.2 mg/ml transfer RNA (Sigma Chemical Co.), 0.8 units/microliter RNAse inhibitor (Promega), 0.4 units per microliter of SP6 Polymerase (NEB). Mutant DNAs were prepared as described by Gottlinger, et al., 1986; Jowett, et al., 1992; Hockley, et al., 1994; or Zhao, et al., 1994; herein incorporated by reference.

2. Translation

Translation of the transcription products was carried out in wheat germ extract containing $^{35}S$ methionine (ICN Pharmaceuticals, Costa Mesa, Calif.). The wheat germ extract was prepared as described by Erickson and Blobel (1983) as modified below. Reactions were performed as previously described (Lingappa, et al., 1994), except for modifications noted below.

A 25 microliter wheat germ transcription/translation reaction mixture contained: 5 microliters Gag transcript (prepared as described in transcription methods), 5 microliters wheat germ extract (prepared as described in wheat germ preparation; preferably using the high speed supernatant detailed in Example 4), 5 microliters 35-S Energy Mix 5X stock (Sigma Chemical Co., St. Louis, Mo.), 2.5 microliters Compensating Buffer (Sigma Chemical Co.), 1.0 microliter 40 mM MgAcetate (Sigma Chemical Co.), 2.0 microliters 125 5M Myristoyl CoA (made up in 20 mM Tris Acetate, pH 7.6; Sigma Chemical Co.), 3.75 microliters 20 mM Tris Acetate buffer, pH 7.6 (U.S. Biochemicals; Cleveland, Ohio), 0.25 microliter Creatine Kinase (4 mg/ml stock in 50% glycerol, 10 mM Tris Acetate; Boehringer Mannheim, Indianapolis, Ind.), 0.25 microliter bovine tRNA (10 mg/ml stock; Sigma Chemical Co.), and 0.25 microliter RNAse Inhibitor (20 units/50; Promega).

3. Preparation of Wheat Germ Extract

Wheat germ was obtained from General Mills. Wheat germ extract was prepared as described by Erickson and Blobel (1983) with modifications indicated: Three grams wheat germ were placed in a mortar and ground in 10 ml homogenization buffer (100 mM K-acetate, 1 mM Mg-acetate, 2 mM $CaCl_2$, 40 mM HEPES buffer, pH 7.5 (Sigma Chemicals, St. Louis, Mo.), 4 mM dithiothreitol) to a thick paste. The homogenate was scraped into a chilled centrifuge tube and centrifuged at 4° for 10 min at 23,000×g. The resulting supernatant was centrifuged again under these conditions to provide an S23 wheat germ extract.

Improved assembly was obtained when the S23 wheat germ extract was further subjected to ultracentrifugation at 50,000 rpm in the TLA 100 rotor (100,000×g) (Beckman Instruments, Palo Alto, Calif.) for 15 min at 4° C. and the supernatant used for in vitro translation. This improvement provided 2–3×the yield obtained in comparable reactions using the S 23 wheat germ extract. This supernatant is referred to herein as a "high speed wheat germ extract supernatant."

Myristoyl coenzyme A (MCoA; Sigma, St. Louis, Mo.) was added at a concentration of 10 micromolar at the start of translation when indicated. Translation reactions ranged in volume from 20 to 100 microliters and were incubated at 25° C. for 150 min. Some reactions were adjusted to a final concentration of the following agents at times indicated in the figures and specification: 0.2 $\mu$M emetine (Sigma); 1.0 units apyrase (Sigma) per mL translation; 0.002%, 0.1%, or 1.0% "NIKKOL". Cell-free translation and assembly reactions were also carried out successfully in rabbit reticulocyte lysate prepared as described previously (Merrick, 1983) or obtained from commercial suppliers (Promega, Madison, Wis.). In pulse-chase experiments, translation reactions contained $^{35}S$ cysteine (Amersham Life Sciences, Cleveland, Ohio) for radiolabeling. After 4 min translation reaction time, 3 mM unlabeled cysteine was added, and the reaction was continued at 25° C. for variable chase times as indicated in the experiments described herein.

D. Estimation of Sedimentation Coefficients

Estimates of S-values of Gag-containing complexes seen on 13 ml sucrose gradients were determined by the method of McEwen (1967) using the following formula:

$$S = \Delta I / \omega^2 t$$

where S is the sedimentation coefficient of the particle in Svedberg units, $\Delta I$ is the time integral for sucrose at the separated zone minus the time integral for sucrose at the meniscus of the gradient, $\omega$ is rotor speed in radians/sec, and t is time in sec.

Values for I were determined for particles of a density of 1.3 g/cm3 and for a temperature of 5° C., according to tables published by McEwen (1967). Calculated S values for different fractions in the gradients are labeled as markers above each gradient tracing shown herein. Markers such as BSA (5-S), macroglobulin (20-S), Hepatitis B Virus capsids (100-S), ribosomal subunits (40-S and 60-S), and polysomes (>100-S) were used to calibrate the gradients and to confirm the calculated S values. However, it should be noted that the S value assignments for each Gag-containing complex are approximate estimates and may vary by about ±10%.

Example 2

Preparation of HSS, HSP, and HSPd

Where indicated, wheat germ extract prepared as described in Example 1 was centrifuged at either 50,000 rpm for 21 min or 100,000 rpm for 30 min in a TLA 100 rotor (Beckman Instruments, Palo Alto, Calif.). The supernatant (HSS) of the 50,000 rpm spin was used for cell-free translation and assembly reactions. The pellet of the 100,000 rpm spin (HSP) was resuspended at a 5×concentration in buffer (25 mM Hepes pH 7.4, 4 mM MgAc, 100 mM KAc, 0.25M sucrose). Wheat germ extract adjusted to contain a concentration 0.5% "NIKKOL" was subjected to the same ultracentrifugation in parallel to generate the detergent treated high speed pellet (HSPd). This pellet was washed twice with 200 $\mu$L of the above non-detergent buffer in order to remove traces of detergent, and then resuspended as described above. Following treatment with emetine at 50 min, 1.8 µL of HSP or HSPd was added to the 18 mL cell-free reactions programmed with HSS. Control reactions were treated with the same volume of buffer at the same time. At the end of the 150 min incubation, reactions were separated into soluble and particulate fractions and analyzed as described above.

Example 3

Transfections and Production of Authentic Capsids

Cos-1 cells (University of California Cell Culture Facility) were transfected by the adenovirus-based method (Forsayeth and Garcia, 1994), using plasmids pSVGagRRE-R (a mammalian expression vector that encodes Gag as well as the Rev response element required for expression of Gag in mammalian cells) and pSVRev (a mammalian expression vector that encodes the Rev gene, the product of which is required for expression of Gag in mammalian cells) (Smith, et al., 1993). These vectors were provided by D. Rekosh (University of Virginia). Four days after transfection, immature HIV particles were purified from the culture medium by sedimentation through a 4 ml 20% sucrose cushion in an SW 40 rotor at 29,000 rpm for 120 min (Mergener, et al., 1992). The pellet was harvested, stored in aliquots at −80° C., and treated with 1% NP40 buffer just before use to remove envelopes. These de-enveloped authentic immature HIV capsids were used as standards and analyzed in parallel with the products of cell-free reactions by a variety of methods, including velocity sedimentation, equilibrium centrifugation, and electron microscopy.

A lysate of transfected Cos cells was prepared by solubilizing transfected cells on 60 mm plates in 700 µL 1% NP40 buffer. This detergent lysate was passaged 20 times through a 20-gauge needle, clarified by centrifugation for 10 min at 2000 ×g, and 150 mL of this supernatant was loaded onto 13 ml sucrose gradients for analysis as described in Example 2. Gag polypeptide present in the fractions was visualized by immunoblotting with a monoclonal antibody to Gag (Dako, Carpenteria, Calif.). Bound antibody was detected using an enhanced chemiluminescence system (Amersham). Band density was determined as described under image analysis below, and relative band densities were confirmed by quantitating films representing different exposure times.

Example 4

Immunoprecipitation of Capsid Assembly Intermediates

Immunoprecipitation under native conditions was performed by diluting 2 µl samples of cell-free reactions into 30 µl of 1% NP40 buffer, and adding approximately 1.0 µg of one of monoclonal antibody 23c (Institute for Cancer Research, London, UK; Stressgen, Vancouver, BC). Samples containing antibodies were incubated for one hour on ice, a 50% slurry of Protein G beads (Pierce, Rockford, Ill.) or Protein A Affigel (BioRad, Richmond, Calif.) was added, and incubations wit constant mixing were performed for one hour at 4° C. Beads were washed twice in 1% NP 40 buffer containing 0.1 M Tris, pH 8.0, and then twice in wash buffer (0.1 M NaCl, 0.1 M Tris, pH 8.0, 4 mM MgAc). Proteins were eluted from the beads by boiling in 20 µl SDS sample buffer and were visualized by SDS-PAGE and autoradiography, according to methods well known in the art.

All patent and literature references cited herein are incorporated herein in their entireties.

While the invention has been described with reference to specific methods and embodiments, it will be appreciated that various modifications and changes may be made without departing from the invention.

It is claimed:

1. A cell-free system for translation and assembly of an HIV capsid, comprising:

a cell-free translation mixture which contains a cell-free extract comprising a eukaryotic cell component of a high speed pellet, amino acids, transfer RNA (tRNA), ribosomes, and an energy source, an mRNA molecule encoding a Gag Pr55 protein derived from human immunodeficiency virus (HIV), and myristoyl coenzyme A, wherein said eukaryotic cell component is characterized by insensitivity to a concentration of at least 0.5% (wt/vol) octaethyleneglycol mono n-dodecyl ether detergent, wherein said eukaryotic cell component comprises a host assembly protein which is a 68 kilodalton that is present in a detergent treated high speed pellet of a wheat germ extract or a protein having the structure of said 68 kilodalton protein, and wherein said protein provides for capsid assembly in said cell-free system when said HIV Pr55 mRNA Gag protein is wild type.

2. The cell-free translation system according to claim 1, which further includes a detergent-sensitive fraction derived from eukaryotic cell membranes.

3. The cell-free translation system according to claim 1, wherein said eukaryotic cell component comprises one or more host assembly protein that is immunoreactive with antibody 23c and forms one or more complex with said Gag protein.

4. The cell-free translation system according to claim 1, which further includes (i) a DNA molecule which encodes HIV Gag Pr55, (ii) an RNA polymerase for synthesizing said mRNA, and (iii) sufficient concentrations of nucleotides ATP, UTP, GTP, and CTP to support such mRNA synthesis.

5. The cell-free translation system according to claim 1, wherein said HIV Gag mRNA encodes a mutant defective in assembly.

6. The cell-free translation system according to claim 1, wherein said concentration of myristoyl coenzyme A is between about 5 and 30 micromolar.

7. The cell free system according to claim 1, wherein said concentration of myristoyl coenzyme A is between about 0.01 and 100 micromolar.

8. A method for producing an HIV capsid intermediate in a cell-free system, said method comprising:

adding to a cell-free protein translation mixture which contains a cell-free extract comprising a eukaryotic cell component of a high speed pellet, amino acids, transfer RNA (tRNA), ribosomes, and an energy source: (i) an mRNA molecule encoding an HIV Pr55 mRNA Gag protein, and (ii) a concentration of myristoyl coenzyme A that is greater than about 0.1 micromolar, to form a reaction mixture; wherein said eukaryotic cell component is characterized by insensitivity to a concentration of at least 0.5% (wt/vol) octaethyleneglycol mono n-dodecyl ether detergent, wherein said eukaryotic cell component comprises a host assembly protein which is a 68 kilodalton that is present in a detergent treated high speed pellet of a wheat germ extract or a protein having the structure of said 68 kilodalton host assembly protein, and wherein said protein provides for capsid assembly in said cell-free system when said HIV Pr55 mRNA Gag protein is wild type; and incubating said reaction mixture for a period of time sufficient to assemble Gag Pr55 mRNA translation products into one or more HIV capsid intermediate.

9. The method according to claim 8, wherein said cell-free extract comprises a detergent-sensitive fraction derived from eukaryotic cell membranes.

10. The method according to claim 8, wherein said host assembly protein comprises a peptide region having the sequence shown in SEQ.ID.NO.: 2 and C-terminal epitope LDD-COOH.

11. The method according to claim 8, which further includes adding to said reaction a Gag Pr55 DNA transcript and a transcription mixture containing an RNA polymerase and ribonucleotides ATP, UTP, GTP and CTP effective to produce said Gag mRNA in said cell-free mixture.

* * * * *

UNITED STATES PATENT AND TRADEMARK OFFICE
CERTIFICATE OF CORRECTION

PATENT NO. : 6,593,103 B1
DATED : July 15, 2003
INVENTOR(S) : Lingappa et al.

It is certified that error appears in the above-identified patent and that said Letters Patent is hereby corrected as shown below:

Column 3,
Line 26, after "used to design", delete "of";
Line 44, after "myristoyl coenzyme A" insert -- (MCoA) --;
Line 54, after "translation mixture", insert -- can --.

Column 4,
Line 8, before "mRMA", delete "said";
Line 8, after "mRNA", insert -- encoding an HIV Pr55 Gag protein --;
Line 39, replace "compared" with -- and the results --;
Line 40, after "compound", insert -- compared --;
Line 52, after "characterized by", insert -- an --;
Line 66, replace "provide" with -- providing --.

Column 5,
Line 1, replace "to alter" with -- in altering --;
Line 5, after "compared to", insert -- that or --;
Line 6, after "selected if", delete "if";
Line 8, replace "the" with -- that of --;
Line 16, after "HIV RNA or", insert -- an --;
Line 36, after ""NIKKOL"", insert -- (2B )--;
Line 52, replace "$^{35}$S cysteine" with -- $^{35}$S-cysteine --;
Line 56, after "radiography", insert -- (AR) --;
Line 57, replace "shows" with -- show --;
Line 64, replace "encoding Pr55 cDNA" with -- containing cDNA encoding Pr55 --.

Column 6,
Line 5, after "arrested, ", insert -- as --;
Line 16, after "translation", delete "20";
Line 21, after "mixture", delete "which";
Line 50, replace "S23wheat" with -- S23 wheat --.

Column 7,
Line 8, replace "by adding to cells" with -- addition to cells of --.

UNITED STATES PATENT AND TRADEMARK OFFICE
CERTIFICATE OF CORRECTION

PATENT NO. : 6,593,103 B1
DATED : July 15, 2003
INVENTOR(S) : Lingappa et al.

It is certified that error appears in the above-identified patent and that said Letters Patent is hereby corrected as shown below:

Column 8,
Line 65, replace "EukarEotic" with -- Eukaryotic --.

Column 9,
Line 50, replace "$^{35}$S methionine" with -- $^{35}$S-methionine --.

Column 11,
Line 46, replace "sensitive" with -- sensitivity --;
Line 62, after "start", insert -- of the --;

Column 12,
Line 25, replace "though" with -- although --,;
Line 47, after "data provide", insert -- a --.

Column 13,
Line 1, after "bar graph", insert -- in Fig. 3A --.

Column 14,
Line 44, after "subtracting", delete "of".

Column 15,
Line 25, after "fractionated", replace "on" with -- by --.

Column 16,
Line 14, replace "$^{35}$S cysteine" with -- $^{35}$S-cysteine --.

Column 19,
Line 4, replace "inimunoreactivity" with -- immunoreactivity --;
Line 7, replace "35-S cysteine" with -- $^{35}$S-cysteine --.

Column 20,
Line 23, before "(i)", delete "is".

UNITED STATES PATENT AND TRADEMARK OFFICE
CERTIFICATE OF CORRECTION

PATENT NO.    : 6,593,103 B1
DATED         : July 15, 2003
INVENTOR(S)   : Lingappa et al.

It is certified that error appears in the above-identified patent and that said Letters Patent is hereby corrected as shown below:

Column 21,
Lines 17 and 27, replace "resembling" with -- and that resembled --;

Column 23,
Lines 3-4, replace "35-S methionine" with -- $^{35}$S-methionine --;
Line 33, replace "$^{35}$S methionine" with -- $^{35}$S-methionine --;
Line 67, replace "S23wheat" with -- S23 wheat --.

Column 24,
Line 1, replace "S23wheat" with -- S23 wheat --;
Line 6, replace "2-3xthe" with -- 2-3 fold the- --
Line 7, replace "S 23wheat" with -- S23 wheat --;
Line 17, replace "units" with -- unit --;
Line 23, replace "$^{35}$S cysteine" with -- $^{35}$S-cysteine--;
Line 61, replace "5xconcentration" with -- 5X concentration --.

Column 26,
Line 19, before "monoclonal", delete "one of";
Line 24, replace "wit" with --with --.

Signed and Sealed this

First Day of June, 2004

JON W. DUDAS
*Acting Director of the United States Patent and Trademark Office*